(12) United States Patent  
Kanaya et al.

(10) Patent No.: US 8,535,928 B2
(45) Date of Patent: Sep. 17, 2013

(54) PROTEASE AND USE THEREOF

(75) Inventors: Shigenori Kanaya, Suita (JP); Tita Foophow, Suita (JP); Kazufumi Takano, Suita (JP); Yuichi Koga, Suita (JP)

(73) Assignee: Osaka University, Osaka (JP)

( * ) Notice: Subject to any disclaimer, the term of this patent is extended or adjusted under 35 U.S.C. 154(b) by 223 days.

(21) Appl. No.: 13/055,828

(22) PCT Filed: Jul. 30, 2009

(86) PCT No.: PCT/JP2009/063547
§ 371 (c)(1),
(2), (4) Date: Feb. 10, 2011

(87) PCT Pub. No.: WO2010/013767
PCT Pub. Date: Feb. 4, 2010

(65) Prior Publication Data
US 2011/0143421 A1    Jun. 16, 2011

(30) Foreign Application Priority Data
Jul. 31, 2008   (JP) ................................. 2008-197467

(51) Int. Cl.
*C12N 9/48*     (2006.01)
*C12N 15/00*    (2006.01)
*C12P 21/04*    (2006.01)
*C12P 21/06*    (2006.01)
*C11D 3/386*    (2006.01)
*C07H 21/04*    (2006.01)

(52) U.S. Cl.
USPC ......... 435/212; 435/440; 435/69.1; 435/71.1; 510/114; 536/23.2

(58) Field of Classification Search
None
See application file for complete search history.

(56) References Cited

U.S. PATENT DOCUMENTS

| | | | |
|---|---|---|---|
| 5,643,777 A * | 7/1997 | Antranikian et al. ......... 435/220 |
| 6,261,822 B1 | 7/2001 | Takakura et al. |
| 6,358,726 B1 | 3/2002 | Takakura et al. |
| 6,783,970 B2 | 8/2004 | Takakura et al. |
| 6,849,441 B2 | 2/2005 | Takakura et al. |
| 7,144,719 B2 | 12/2006 | Takakura et al. |
| 7,314,744 B2 | 1/2008 | Takakura et al. |
| 2002/0086402 A1 | 7/2002 | Takakura et al. |
| 2002/0132335 A1 | 9/2002 | Takakura et al. |
| 2005/0014221 A1 | 1/2005 | Takakura et al. |
| 2005/0084934 A1 | 4/2005 | Takakura et al. |
| 2006/0248617 A1 | 11/2006 | Imanaka et al. |
| 2009/0029416 A1 | 1/2009 | Takakura et al. |

FOREIGN PATENT DOCUMENTS

| | | |
|---|---|---|
| JP | 2007-006846 | 1/2007 |
| WO | 97/21823 | 6/1997 |
| WO | 98/56926 | 12/1998 |

OTHER PUBLICATIONS

Q5JIZ5. UnitProtKB Database. Jul. 22, 2008.*
BAD85878. EMBL Database. May 19, 2007.*
Current Protocols in Protein Science. John Wiley & Sons, Inc. 5.1-5.1.8. 1995.*
Sambrook et al. Molecular Cloning, 1989, Cold Spring Harbor Laboratory Press, pp. 8.46-8.52 and pp. 11.2-11.19.*
Branden et al. Introduction to Protein Structure, Garland Publishing Inc., New York, p. 247, 1991.*
International Preliminary Report on Patentability (English Translation) issued Apr. 21, 2011 in corresponding International (PCT) Application No. PCT/JP2009/063547.
Extended European Search Report issued Apr. 16, 2012 in corresponding European Application No. 09803009.1.
Fukui, Toshiaki, et al., "Complete genome sequence of the hyperthermophilic archaeon *Thermococcus kodakaraensis* KOD1 and comparison with *Pyrococcus* genomes", Cold Spring Harbor Laboratory Press, vol. 15, No. 3, Mar. 2005, pp. 352-363.
Foophow, Tita, "Crystal Structure of a Subtilisin Homologue, Tk-SP, from *Thermococcus kodakaraensis*: Requirement of a C-terminal β-Jelly Roll Domain for Hyperstability", J. Mol. Biol., vol. 400, No. 4, Jul. 2010, pp. 865-877.
International Search Report issued Oct. 6, 2009 in International (PCT) Application No. PCT/JP2009/063547.
Y. Kannan et al., "Active Subtilisin-Like Protease from a Hyperthermophilic Archaeon in a Form with a Putative Prosequence", Applied and Environmental Microbiology, vol. 67, No. 6, pp. 2445-2452, Jun. 2001.
M. Pulido et al., "$Ca^{2+}$-Dependent Maturation of Subtilism from a Hyperthermophilic Archaeon, *Thermococcus kodakaraensis*: the Propeptide is a Potent Inhibitor of the Mature Domain but is not Required for its Folding", Applied and Environmental Microbiology, vol. 72, No. 6, pp. 4154-4162, Jun. 2006.
M. A. Pulido et al., "Directed Evolution of Tk-Subtilisin from a Hyperthermophilic Archaeon: Identification of a Single Amino Acid Substitution Responsible for Low-Temperature Adaption", Protein Engineering, Design & Selection, vol. 20, No. 3, pp. 143-153, 2007.
S. Tanaka et al., "Crystal Structure of Unautoprocessed Precursor of Subtilisin from a Hyperthermophilic Archaeon", The Journal of Biological Chemistry, vol. 282, No. 11, pp. 8246-8255, Mar. 16, 2007.
S. Tanaka et al., "Four New Crystal Structures of Tk-Subtilisin in Unautoprocessed, Autoprocessed and Mature Forms: Insight into Structural Changes during Maturation", J. Mol. Biol., vol. 372, pp. 1055-1069, 2007.

(Continued)

*Primary Examiner* — Yong Pak
(74) *Attorney, Agent, or Firm* — Wenderoth, Lind & Ponack, L.L.P.

(57) ABSTRACT

A novel protease comprising any one of
(a) the amino acid sequence of SEQ ID NO: 1,
(b) an amino acid sequence having deletion, substitution or addition of one to several amino acids in the amino acid sequence of SEQ ID NO: 1,
(c) the amino acid sequence of SEQ ID NO: 3, and
(d) an amino acid sequence having deletion, substitution or addition of one to several amino acids in the amino acid sequence of SEQ ID NO: 3, has a high activity under high temperature and high alkaline conditions, a high stability to protein denaturants and surfactants and high effectiveness as a protease used in detergents.

8 Claims, 6 Drawing Sheets

(56) References Cited

OTHER PUBLICATIONS

M. A. Pulido et al., "Requirement of Left-Handed Glycine Residue for High Stability of the Tk-Subtilisin Propeptide as Revealed by Mutational and Crystallographic Analysis", J. Mol. Biol., vol. 374, pp. 1359-1373, 2007.

T. Fukui et al., Definition: Subtilisin-like serine protease, Database DDBJ/EMBL/GenBank [online], Oct. 31, 2006, Accession No. Q5J1Z5, http://www.ncbi.nlm.nih.gov/protein/74506265.

* cited by examiner

TK-Sp TITA    a sheet of PVDF membrane

| Cycle | AA | p mol | AA | p mol | |
|---|---|---|---|---|---|
| 1 | V | 6.76 | T | 2.26 | |
| 2 | E | 4.52 | V | 3.59 | L,I,P |
| 3 | T | 7.40 | G | 3.15 | Q,E,F |
| 4 | E | 3.72 | T | 2.75 | V,Y,N |

VETE

■ = 80C, ▲ = 90C, ○ = 100C

SEQUENCE LISTING

<160> NUMBER OF SEQ ID NOS: 10

<210> SEQ ID NO 1
<211> LENGTH: 426
<212> TYPE: PRT
<213> ORGANISM: Thermococcus kodakaraensis

<400> SEQUENCE: 1

```
Val Glu Thr Glu Gly Leu Asp Glu Ser Ala Ala Gln Val Met Ala Thr
 1               5                  10                  15

Asn Met Trp Asn Leu Gly Tyr Asp Gly Ser Gly Ile Thr Ile Gly Ile
             20                  25                  30

Ile Asp Thr Gly Ile Asp Ala Ser His Pro Asp Leu Gln Gly Lys Val
         35                  40                  45

Ile Gly Trp Val Asp Phe Val Asn Gly Lys Thr Thr Pro Tyr Asp Asp
     50                  55                  60

Asn Gly His Gly Thr His Val Ala Ser Ile Ala Ala Gly Thr Gly Ala
 65                  70                  75                  80

Ala Ser Asn Gly Lys Tyr Lys Gly Met Ala Pro Gly Ala Lys Leu Val
                 85                  90                  95

Gly Ile Lys Val Leu Asn Gly Gln Gly Ser Gly Ser Ile Ser Asp Ile
            100                 105                 110

Ile Asn Gly Val Asp Trp Ala Val Gln Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ser Leu Ser Gln Ala Val Asn Asn Ala Trp Asp Ala Gly Leu Val
145                 150                 155                 160

Val Val Val Ala Ala Gly Asn Ser Gly Pro Asn Lys Tyr Thr Val Gly
                165                 170                 175

Ser Pro Ala Ala Ala Ser Lys Val Ile Thr Val Gly Ala Val Asp Lys
            180                 185                 190

Tyr Asp Val Ile Thr Asp Phe Ser Arg Gly Pro Thr Ala Asp Asn
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ala Tyr
    290                 295                 300

Tyr Asp Asn Tyr Ala Lys Leu Thr Phe Thr Gly Tyr Val Ser Asn Lys
305                 310                 315                 320

Gly Ser Gln Ser His Gln Phe Thr Ile Ser Gly Ala Gly Phe Val Thr
                325                 330                 335

Ala Thr Leu Tyr Trp Asp Asn Ser Gly Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365
```

Gly Phe Glu Lys Val Gly Tyr Tyr Asn Pro Thr Ala Gly Thr Trp Thr
            370                 375                 380

Ile Lys Val Val Ser Tyr Ser Gly Ser Ala Asn Tyr Gln Val Asp Val
385                 390                 395                 400

Val Ser Asp Gly Ser Leu Gly Gln Pro Ser Gly Gly Ser Glu Pro
                405                 410                 415

Ser Pro Ser Pro Ser Pro Glu Pro Thr Val
            420                 425

<210> SEQ ID NO 2
<211> LENGTH: 1278
<212> TYPE: DNA
<213> ORGANISM: Thermococcus kodakaraensis

<400> SEQUENCE: 2
gttgagaccg agggtctcga cgagtccgct gcccaggtta tggccaccaa catgtggaac      60
ctcggctacg acggttccgg aataaccatc ggtatcatcg acaccggtat tgacgcctcc     120
caccccgatc tccagggcaa ggttatcgga tgggttgact tcgtcaacgg aaagacaact     180
ccctacgacg acaacggcca cggaacccac gtcgcttcga tagccgccgg aaccggtgcg     240
gcaagcaacg gcaagtacaa gggtatggcc ccaggcgcca agctcgttgg cattaaggtt     300
ctcaacggtc agggaagcgg aagcatctca gacatcatca acggtgttga ctgggctgtc     360
cagaacaagg acaagtacgg aataaaggtc attaacctct cccttggctc aagccagagc     420
tccgacggta ccgactccct cagccaggcc gtcaacaacg cctgggacgc cggacttgtc     480
gtcgttgtgg ctgctggaaa cagtgggccg aacaagtaca cagtgggctc accggcagcg     540
gccagcaagg tcatcaccgt cggtgcggtt gacaagtacg acgtcataac cgacttctca     600
agccgcggcc aacagccgac aacaggctca agccagagg tcgttgctcc gggcaactgg     660
atcatcgctg cccgcgccag cggaaccagc atgggacagc cgataaacga ttactacacc     720
gccgctccag gaacctcgat ggccactcca cacgtcgctg gtatagccgc ccttctcctc     780
caggcccacc cgagctggac tcccgacaag gtcaagacgg ccctcatcga gaccgccgac     840
atagtaaagc ccgacgagat agccgacatc gcctacggtg caggtagggt caacgcctat     900
aaggctgcct actacgacaa ctatgcaaag ctcaccttca ctggatacgt ctcaaacaag     960
ggaagccaga gccaccagtt cacgataagc ggtgctggat tcgtcacggc aaccctctac    1020
tgggacaaca gcggaagcga cctcgacctc tacctctacg acccgaacgg caaccaggtt    1080
gactactcct acaccgccta ctacggcttc gaaaaggtcg gctactacaa cccgacagca    1140
ggaacctgga cgataaaggt cgtcagctac agcggttcgg caaactacca ggttgacgtc    1200
gtcagcgacg ggagcctcgg ccagcccagc ggtggcggaa gcgagccgag cccgagcccc    1260
tcaccagagc cgaccgtt                                                 1278

<210> SEQ ID NO 3
<211> LENGTH: 427
<212> TYPE: PRT
<213> ORGANISM: Thermococcus kodakaraensis

<400> SEQUENCE: 3

Val Glu Thr Glu Gly Leu Asp Glu Ser Ala Ala Gln Val Met Ala Thr
1               5                   10                  15

Asn Met Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val

```
            35                  40                  45
Ile Gly Trp Val Asp Phe Val Asn Gly Lys Thr Thr Pro Tyr Asp Asp
 50                  55                  60

Asn Gly His Gly Thr His Val Ala Ser Ile Ala Ala Gly Thr Gly Ala
 65                  70                  75                  80

Ala Ser Asn Gly Lys Tyr Lys Gly Met Ala Pro Gly Ala Lys Leu Val
                 85                  90                  95

Gly Ile Lys Val Leu Asn Gly Gln Gly Ser Gly Ser Ile Ser Asp Ile
100                 105                 110

Ile Asn Gly Val Asp Trp Ala Val Gln Asn Lys Asp Lys Tyr Gly Ile
            115                 120                 125

Lys Val Ile Asn Leu Ser Leu Gly Ser Ser Gln Ser Ser Asp Gly Thr
130                 135                 140

Asp Ser Leu Ser Gln Ala Val Asn Asn Ala Trp Asp Ala Gly Leu Val
145                 150                 155                 160

Val Val Val Ala Ala Gly Asn Ser Gly Pro Asn Lys Tyr Thr Val Gly
                165                 170                 175

Ser Pro Ala Ala Ala Ser Lys Val Ile Thr Val Gly Ala Val Asp Lys
            180                 185                 190

Tyr Asp Val Ile Thr Asp Phe Ser Ser Arg Gly Pro Thr Ala Asp Asn
            195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
            275                 280                 285

Asp Ile Ala Tyr Gly Ala Gly Arg Val Asn Ala Tyr Lys Ala Ala Tyr
290                 295                 300

Tyr Asp Asn Tyr Ala Lys Leu Thr Phe Thr Gly Tyr Val Ser Asn Lys
305                 310                 315                 320

Gly Ser Gln Ser His Gln Phe Thr Ile Ser Gly Ala Gly Phe Val Thr
                325                 330                 335

Ala Thr Leu Tyr Trp Asp Asn Ser Gly Ser Asp Leu Asp Leu Tyr Leu
            340                 345                 350

Tyr Asp Pro Asn Gly Asn Gln Val Asp Tyr Ser Tyr Thr Ala Tyr Tyr
            355                 360                 365

Gly Phe Glu Lys Val Gly Tyr Tyr Asn Pro Thr Ala Gly Thr Trp Thr
370                 375                 380

Ile Lys Val Val Ser Tyr Ser Gly Ser Ala Asn Tyr Gln Val Asp Val
385                 390                 395                 400

Val Ser Asp Gly Ser Leu Gly Gln Pro Ser Gly Gly Ser Glu Pro
                405                 410                 415

Ser Pro Ser Pro Ser Pro Glu Pro Thr Val Asp
            420                 425

<210> SEQ ID NO 4
<211> LENGTH: 1281
<212> TYPE: DNA
<213> ORGANISM: Thermococcus kodakaraensis
```

```
<400> SEQUENCE: 4
gttgagaccg agggtctcga cgagtccgct gcccaggtta tggccaccaa catgtggaac     60
ctcggctacg acggttccgg aataaccatc ggtatcatcg acaccggtat tgacgcctcc    120 cacccccgatc tccagggcaa ggttatcgga tgggttgact tcgtcaacgg aaagacaact   180
ccctacgacg acaacggcca cggaacccac gtcgcttcga tagccgccgg aaccggtgcg   240
gcaagcaacg gcaagtacaa gggtatggcc ccaggcgcca agctcgttgg cattaaggtt   300
ctcaacggtc agggaagcgg aagcatctca gacatcatca acggtgttga ctgggctgtc   360
cagaacaagg acaagtacgg aataaaggtc attaacctct cccttggctc aagccagagc   420
tccgacggta ccgactccct cagccaggcc gtcaacaacg cctgggacgc cggacttgtc   480
gtcgttgtgg ctgctggaaa cagtgggccg aacaagtaca cagtgggctc accggcagcg   540
gccagcaagg tcatcaccgt cggtgcggtt gacaagtacg acgtcataac cgacttctca   600
agccgcggcc caacagccga caacaggctc aagccagagg tcgttgctcc gggcaactgg   660
atcatcgctg cccgcgccag cggaaccagc atgggacagc cgataaacga ttactacacc   720
gccgctccag gaacctcgat ggccactcca cacgtcgctg gtatagccgc ccttctcctc   780
caggcccacc cgagctggac tcccgacaag gtcaagacgg ccctcatcga gaccgccgac   840
atagtaaagc ccgacgagat agccgacatc gcctacggtg caggtagggt caacgcctat   900
aaggctgcct actacgacaa ctatgcaaag ctcaccttca ctggatacgt ctcaaacaag   960
ggaagccaga gccaccagtt cacgataagc ggtgctggat tcgtcacggc aaccctctac  1020
tgggacaaca gcggaagcga cctcgacctc tacctctacg acccgaacgg caaccaggtt  1080
gactactcct acaccgccta ctacggcttc gaaaaggtcg gctactacaa cccgacagca  1140
ggaacctgga cgataaaggt cgtcagctac agcggttcgg caaactacca ggttgacgtc  1200
gtcagcgacg ggagcctcgg ccagcccagc ggtggcggaa gcgagccgag cccgagcccc  1260
tcaccagagc cgaccgttga c                                            1281

<210> SEQ ID NO 5
<211> LENGTH: 640
<212> TYPE: PRT
<213> ORGANISM: Thermococcus kodakaraensis

<400> SEQUENCE: 5

Ala Pro Gln Lys Pro Ala Val Arg Asn Val Ser Gln Gln Lys Asn Tyr
1               5                   10                  15

Gly Leu Leu Thr Pro Gly Leu Phe Lys Lys Val Gln Arg Met Ser Trp
            20                  25                  30

Asp Gln Glu Val Ser Thr Ile Ile Met Phe Asp Asn Gln Ala Asp Lys
        35                  40                  45

Glu Lys Ala Val Glu Ile Leu Asp Phe Leu Gly Ala Lys Ile Lys Tyr
    50                  55                  60

Asn Tyr His Ile Ile Pro Ala Leu Ala Val Lys Ile Lys Val Lys Asp
65                  70                  75                  80

Leu Leu Ile Ile Ala Gly Leu Met Asp Thr Gly Tyr Phe Gly Asn Ala
                85                  90                  95

Gln Leu Ser Gly Val Gln Phe Ile Gln Glu Asp Tyr Val Val Lys Val
            100                 105                 110

Ala Val Glu Thr Glu Gly Leu Asp Glu Ser Ala Ala Gln Val Met Ala
        115                 120                 125

Thr Asn Met Trp Asn Leu Gly Tyr Asp Gly Ser Gly Ile Thr Ile Gly
    130                 135                 140
```

```
Ile Ile Asp Thr Gly Ile Asp Ala Ser His Pro Asp Leu Gln Gly Lys
145                 150                 155                 160

Val Ile Gly Trp Val Asp Phe Val Asn Gly Lys Thr Thr Pro Tyr Asp
                165                 170                 175

Asp Asn Gly His Gly Thr His Val Ala Ser Ile Ala Ala Gly Thr Gly
            180                 185                 190

Ala Ala Ser Asn Gly Lys Tyr Lys Gly Met Ala Pro Gly Ala Lys Leu
        195                 200                 205

Val Gly Ile Lys Val Leu Asn Gly Gln Gly Ser Gly Ser Ile Ser Asp
    210                 215                 220

Ile Ile Asn Gly Val Asp Trp Ala Val Gln Asn Lys Asp Lys Tyr Gly
225                 230                 235                 240

Ile Lys Val Ile Asn Leu Ser Leu Gly Ser Ser Gln Ser Ser Asp Gly
                245                 250                 255

Thr Asp Ser Leu Ser Gln Ala Val Asn Asn Ala Trp Asp Ala Gly Leu
            260                 265                 270

Val Val Val Val Ala Ala Gly Asn Ser Gly Pro Asn Lys Tyr Thr Val
        275                 280                 285

Gly Ser Pro Ala Ala Ala Ser Lys Val Ile Thr Val Gly Ala Val Asp
    290                 295                 300

Lys Tyr Asp Val Ile Thr Asp Phe Ser Ser Arg Gly Pro Thr Ala Asp
305                 310                 315                 320

Asn Arg Leu Lys Pro Glu Val Val Ala Pro Gly Asn Trp Ile Ile Ala
                325                 330                 335

Ala Arg Ala Ser Gly Thr Ser Met Gly Gln Pro Ile Asn Asp Tyr Tyr
            340                 345                 350

Thr Ala Ala Pro Gly Thr Ser Met Ala Thr Pro His Val Ala Gly Ile
        355                 360                 365

Ala Ala Leu Leu Leu Gln Ala His Pro Ser Trp Thr Pro Asp Lys Val
    370                 375                 380

Lys Thr Ala Leu Ile Glu Thr Ala Asp Ile Val Lys Pro Asp Glu Ile
385                 390                 395                 400

Ala Asp Ile Ala Tyr Gly Ala Gly Arg Val Asn Ala Tyr Lys Ala Ala
                405                 410                 415

Tyr Tyr Asp Asn Tyr Ala Lys Leu Thr Phe Thr Gly Tyr Val Ser Asn
            420                 425                 430

Lys Gly Ser Gln Ser His Gln Phe Thr Ile Ser Gly Ala Gly Phe Val
        435                 440                 445

Thr Ala Thr Leu Tyr Trp Asp Asn Ser Gly Ser Asp Leu Asp Leu Tyr
    450                 455                 460

Leu Tyr Asp Pro Asn Gly Asn Gln Val Asp Tyr Ser Tyr Thr Ala Tyr
465                 470                 475                 480

Tyr Gly Phe Glu Lys Val Gly Tyr Tyr Asn Pro Thr Ala Gly Thr Trp
                485                 490                 495

Thr Ile Lys Val Val Ser Tyr Ser Gly Ser Ala Asn Tyr Gln Val Asp
            500                 505                 510

Val Val Ser Asp Gly Ser Leu Gly Gln Pro Ser Gly Gly Gly Ser Glu
        515                 520                 525

Pro Ser Pro Ser Pro Ser Pro Glu Pro Thr Val Asp Glu Lys Thr Phe
    530                 535                 540

Thr Gly Thr Val His Asp Tyr Tyr Asp Lys Ser Asp Thr Phe Thr Met
545                 550                 555                 560

Thr Val Asn Ser Gly Ala Thr Lys Ile Thr Gly Asp Leu Tyr Phe Asp
```

565                 570                 575
Thr Ser Tyr His Asp Leu Asp Leu Tyr Leu Tyr Asp Pro Asn Gln Asn
            580                 585                 590

Leu Val Asp Arg Ser Glu Ser Ser Asn Ser Tyr Glu His Val Glu Tyr
        595                 600                 605

Asn Asn Pro Ala Pro Gly Thr Trp Tyr Phe Leu Val Tyr Ala Tyr Asp
    610                 615                 620

Thr Tyr Gly Tyr Ala Asp Tyr Gln Leu Asp Ala Lys Val Tyr Tyr Gly
625                 630                 635                 640

<210> SEQ ID NO 6
<211> LENGTH: 1923
<212> TYPE: DNA
<213> ORGANISM: Thermococcus kodakaraensis

<400> SEQUENCE: 6

| | | | | |
|---|---|---|---|---|
| gccccccaga | agccggcagt | tcgcaatgtt | tcccagcaga | agaactatgg | tcttctcacc | 60 |
| cctggactct | tcaagaaagt | ccagagaatg | agctgggatc | aggaagttag | cacgataata | 120 |
| atgttcgaca | atcaggccga | caaggagaag | gccgttgaaa | tactggactt | ccttggagcc | 180 |
| aagatcaaat | acaactacca | cattatcccc | gccctcgcag | tcaagataaa | ggttaaggat | 240 |
| cttcttataa | tcgccggcct | tatggacacc | ggctactttg | aaacgcaca | gctctcaggt | 300 |
| gtccagttca | tccaggagga | ctacgtggtc | aaggtcgccg | ttgagaccga | gggtctcgac | 360 |
| gagtccgctg | cccaggttat | ggccaccaac | atgtggaacc | tcggctacga | cggttccgga | 420 |
| ataaccatcg | gtatcatcga | caccggtatt | gacgcctccc | accccgatct | ccagggcaag | 480 |
| gttatcggat | gggttgactt | cgtcaacgga | aagacaactc | cctacgacga | caacggccac | 540 |
| ggaacccacg | tcgcttcgat | agccgccgga | accggtgcgg | caagcaacgg | caagtacaag | 600 |
| ggtatggccc | caggcgccaa | gctcgttggc | attaaggttc | tcaacggtca | gggaagcgga | 660 |
| agcatctcag | acatcatcaa | cggtgttgac | tgggctgtcc | agaacaagga | caagtacgga | 720 |
| ataaaggtca | ttaacctctc | ccttggctca | agccagagct | ccgacggtac | cgactccctc | 780 |
| agccaggccg | tcaacaacgc | ctgggacgcc | ggacttgtcg | tcgttgtggc | tgctggaaac | 840 |
| agtgggccga | caagtacac | agtgggctca | ccggcagcgg | ccagcaaggt | catcaccgtc | 900 |
| ggtgcggttg | acaagtacga | cgtcataacc | gacttctcaa | gccgcggccc | aacagccgac | 960 |
| aacaggctca | agccagaggt | cgttgctccg | ggcaactgga | tcatcgctgc | ccgcgccagc | 1020 |
| ggaaccagca | tggacagcc | gataaacgat | tactacaccg | ccgctccagg | aacctcgatg | 1080 |
| gccactccac | acgtcgctgg | tatagccgcc | cttctcctcc | aggcccaccc | gagctggact | 1140 |
| cccgacaagg | tcaagacggc | cctcatcgag | accgccgaca | tagtaaagcc | cgacgagata | 1200 |
| gccgacatcg | cctacggtgc | aggtagggtc | aacgcctata | aggctgccta | ctacgacaac | 1260 |
| tatgcaaagc | tcaccttcac | tggatacgtc | tcaaacaagg | gaagccagag | ccaccagttc | 1320 |
| acgataagcg | gtgctggatt | cgtcacggca | accctctact | gggacaacag | cggaagcgac | 1380 |
| ctcgacctct | acctctacga | cccgaacggc | aaccaggttg | actactccta | caccgcctac | 1440 |
| tacggcttcg | aaaaggtcgg | ctactacaac | ccgacagcag | gaacctggac | gataaaggtc | 1500 |
| gtcagctaca | gcggttcggc | aaactaccag | gttgacgtcg | tcagcgacgg | gagcctcggc | 1560 |
| cagcccagcg | gtgcggaag | cgagccgagc | ccgagcccct | caccagagcc | gaccgttgac | 1620 |
| gagaagacct | tcactggaac | agtccacgac | tactatgata | agagcgacac | attcaccatg | 1680 |
| accgtcaaca | gcggcgccac | caagatcacc | ggcgacctct | acttcgacac | cagctaccat | 1740 |

-continued

```
gacctcgacc tctacctcta cgacccgaac cagaacctcg ttgaccgctc cgagagctcc    1800
aacagctacg agcacgtcga gtacaacaac ccagctccag gaacctggta cttcctcgtc    1860
tacgcctacg ataccatgg ctacgcagac taccaactcg acgccaaggt ttactacggg    1920
tga                                                                  1923
```

<210> SEQ ID NO 7
<211> LENGTH: 663
<212> TYPE: PRT
<213> ORGANISM: Thermococcus kodakaraensis

<400> SEQUENCE: 7

```
Met Lys Lys Phe Gly Ala Val Val Leu Ala Leu Phe Leu Val Gly Leu
1               5                   10                  15

Met Ala Gly Ser Val Leu Ala Ala Pro Gln Lys Pro Ala Val Arg Asn
            20                  25                  30

Val Ser Gln Gln Lys Asn Tyr Gly Leu Leu Thr Pro Gly Leu Phe Lys
        35                  40                  45

Lys Val Gln Arg Met Ser Trp Asp Gln Glu Val Ser Thr Ile Ile Met
    50                  55                  60

Phe Asp Asn Gln Ala Asp Lys Glu Lys Ala Val Glu Ile Leu Asp Phe
65                  70                  75                  80

Leu Gly Ala Lys Ile Lys Tyr Asn Tyr His Ile Ile Pro Ala Leu Ala
                85                  90                  95

Val Lys Ile Lys Val Lys Asp Leu Leu Ile Ile Ala Gly Leu Met Asp
            100                 105                 110

Thr Gly Tyr Phe Gly Asn Ala Gln Leu Ser Gly Val Gln Phe Ile Gln
        115                 120                 125

Glu Asp Tyr Val Val Lys Val Ala Val Glu Thr Glu Gly Leu Asp Glu
    130                 135                 140

Ser Ala Ala Gln Val Met Ala Thr Asn Met Trp Asn Leu Gly Tyr Asp
145                 150                 155                 160

Gly Ser Gly Ile Thr Ile Gly Ile Ile Asp Thr Gly Ile Asp Ala Ser
                165                 170                 175

His Pro Asp Leu Gln Gly Lys Val Ile Gly Trp Val Asp Phe Val Asn
            180                 185                 190

Gly Lys Thr Thr Pro Tyr Asp Asp Asn Gly His Gly Thr His Val Ala
        195                 200                 205

Ser Ile Ala Ala Gly Thr Gly Ala Ala Ser Asn Gly Lys Tyr Lys Gly
    210                 215                 220

Met Ala Pro Gly Ala Lys Leu Val Gly Ile Lys Val Leu Asn Gly Gln
225                 230                 235                 240

Gly Ser Gly Ser Ile Ser Asp Ile Ile Asn Gly Val Asp Trp Ala Val
                245                 250                 255

Gln Asn Lys Asp Lys Tyr Gly Ile Lys Val Ile Asn Leu Ser Leu Gly
            260                 265                 270

Ser Ser Gln Ser Ser Asp Gly Thr Asp Ser Leu Ser Gln Ala Val Asn
        275                 280                 285

Asn Ala Trp Asp Ala Gly Leu Val Val Val Ala Ala Gly Asn Ser
    290                 295                 300

Gly Pro Asn Lys Tyr Thr Val Gly Ser Pro Ala Ala Ser Lys Val
305                 310                 315                 320

Ile Thr Val Gly Ala Val Asp Lys Tyr Asp Val Ile Thr Asp Phe Ser
                325                 330                 335

Ser Arg Gly Pro Thr Ala Asp Asn Arg Leu Lys Pro Glu Val Val Ala
```

```
                340              345              350
Pro Gly Asn Trp Ile Ile Ala Ala Arg Ala Ser Gly Thr Ser Met Gly
            355                  360              365

Gln Pro Ile Asn Asp Tyr Tyr Thr Ala Ala Pro Gly Thr Ser Met Ala
        370                  375              380

Thr Pro His Val Ala Gly Ile Ala Ala Leu Leu Gln Ala His Pro
385                  390              395              400

Ser Trp Thr Pro Asp Lys Val Lys Thr Ala Leu Ile Glu Thr Ala Asp
                405              410              415

Ile Val Lys Pro Asp Glu Ile Ala Asp Ile Ala Tyr Gly Ala Gly Arg
            420                  425              430

Val Asn Ala Tyr Lys Ala Ala Tyr Tyr Asp Asn Tyr Ala Lys Leu Thr
                435              440              445

Phe Thr Gly Tyr Val Ser Asn Lys Gly Ser Gln Ser His Gln Phe Thr
            450                  455              460

Ile Ser Gly Ala Gly Phe Val Thr Ala Thr Leu Tyr Trp Asp Asn Ser
465                  470              475              480

Gly Ser Asp Leu Asp Leu Tyr Leu Tyr Asp Pro Asn Gly Asn Gln Val
                485              490              495

Asp Tyr Ser Tyr Thr Ala Tyr Tyr Gly Phe Glu Lys Val Gly Tyr Tyr
            500                  505              510

Asn Pro Thr Ala Gly Thr Trp Thr Ile Lys Val Ser Tyr Ser Gly
            515                  520              525

Ser Ala Asn Tyr Gln Val Asp Val Val Ser Asp Gly Ser Leu Gly Gln
            530                  535              540

Pro Ser Gly Gly Gly Ser Glu Pro Ser Pro Ser Pro Glu Pro
545                  550              555              560

Thr Val Asp Glu Lys Thr Phe Thr Gly Thr Val His Asp Tyr Tyr Asp
                565              570              575

Lys Ser Asp Thr Phe Thr Met Thr Val Asn Ser Gly Ala Thr Lys Ile
            580                  585              590

Thr Gly Asp Leu Tyr Phe Asp Thr Ser Tyr His Asp Leu Asp Leu Tyr
            595                  600              605

Leu Tyr Asp Pro Asn Gln Asn Leu Val Asp Arg Ser Glu Ser Ser Asn
        610                  615              620

Ser Tyr Glu His Val Glu Tyr Asn Asn Pro Ala Pro Gly Thr Trp Tyr
625                  630              635              640

Phe Leu Val Tyr Ala Tyr Asp Thr Tyr Gly Tyr Ala Asp Tyr Gln Leu
                645              650              655

Asp Ala Lys Val Tyr Tyr Gly
            660

<210> SEQ ID NO 8
<211> LENGTH: 1992
<212> TYPE: DNA
<213> ORGANISM: Thermococcus kodakaraensis

<400> SEQUENCE: 8
atgaagaagt tggagcggt  agtgctggcc ctgttccttg ttggtcttat ggctggcagt      60
gtccttgcag ccccccagaa gccggcagtt cgcaatgttt cccagcagaa gaactatggt    120
cttctcaccc ctggactctt caagaaagtc cagagaatga gctgggatca ggaagttagc    180
acgataataa tgttcgacaa tcaggccgac aaggagaagg ccgttgaaat actggacttc    240
cttggagcca agatcaaata caactaccac attatccccg ccctcgcagt caagataaag    300
```

```
gttaaggatc ttcttataat cgccggcctt atggacaccg gctactttgg aaacgcacag    360
ctctcaggtg tccagttcat ccaggaggac tacgtggtca aggtcgccgt tgagaccgag    420
ggtctcgacg agtccgctgc ccaggttatg gccaccaaca tgtggaacct cggctacgac    480
ggttccggaa taaccatcgg tatcatcgac accggtattg acgcctccca ccccgatctc    540
cagggcaagg ttatcggatg ggttgacttc gtcaacggaa agacaactcc ctacgacgac    600
aacggccacg gaacccacgt cgcttcgata gccgccggaa ccggtgcggc aagcaacggc    660
aagtacaagg gtatggcccc aggcgccaag ctcgttggca ttaaggttct caacggtcag    720
ggaagcggaa gcatctcaga catcatcaac ggtgttgact gggctgtcca gaacaaggac    780
aagtacggaa taaaggtcat taacctctcc cttggctcaa gccagagctc cgacggtacc    840
gactccctca gccaggccgt caacaacgcc tgggacgccg acttgtcgt cgttgtggct    900
gctggaaaca gtgggccgaa caagtacaca gtgggctcac cggcagcggc cagcaaggtc    960
atcaccgtcg gtgcggttga caagtacgac gtcataaccg acttctcaag ccgcggccca   1020
acagccgaca acaggctcaa gccagaggtc gttgctccgg gcaactggat catcgctgcc   1080
cgcgccagcg gaaccagcat gggacagccg ataaacgatt actacaccgc cgctccagga   1140
acctcgatgg ccactccaca cgtcgctggt atagccgccc ttctcctcca ggcccacccg   1200
agctggactc ccgacaaggt caagacggcc ctcatcgaga ccgccgacat agtaaagccc   1260
gacgagatag ccgacatcgc ctacggtgca ggtagggtca acgcctataa ggctgcctac   1320
tacgacaact atgcaaagct caccttcact ggatacgtct caaacaaggg aagccagagc   1380
caccagttca cgataagcgg tgctggattc gtcacggcaa ccctctactg ggacaacagc   1440
ggaagcgacc tcgacctcta cctctacgac ccgaacggca accaggttga ctactcctac   1500
accgcctact acggcttcga aaaggtcggc tactacaacc cgacagcagg aacctggacg   1560
ataaaggtcg tcagctacag cggttcggca aactaccagg ttgacgtcgt cagcgacggg   1620
agcctcggcc agcccagcgg tggcggaagc gagccgagcc cgagcccctc accagagccg   1680
accgttgacg agaagacctt cactggaaca gtccacgact actatgataa gagcgacaca   1740
ttcaccatga ccgtcaacag cggcgccacc aagatcaccg cgacctcta cttcgacacc   1800
agctaccatg acctcgacct ctacctctac gacccgaacc agaacctcgt tgaccgctcc   1860
gagagctcca acagctacga gcacgtcgag tacaacaacc cagctccagg aacctggtac   1920
ttcctcgtct acgcctacga tacctatggc tacgcagact accaactcga cgccaaggtt   1980
tactacgggt ga                                                       1992
```

<210> SEQ ID NO 9
<211> LENGTH: 27
<212> TYPE: DNA
<213> ORGANISM: Artificial Sequence
<220> FEATURE:
<223> OTHER INFORMATION: Synthetic construct; Primer Sequence

<400> SEQUENCE: 9
ggcctttatc atatggcccc ccagaag    27

<210> SEQ ID NO 10
<211> LENGTH: 27
<212> TYPE: DNA
<213> ORGANISM: Artificial Sequence
<220> FEATURE:
<223> OTHER INFORMATION: Synthetic construct; Primer Sequence

```
<400> SEQUENCE: 10
ggccttggat cctcacccgt agtaaac                                                    27
```

PROTEASE AND USE THEREOF

This application is a U.S. national stage of International Application No. PCT/JP2009/063547 filed Jul. 30, 2009.

TECHNICAL FIELD

The present invention relates to a novel protease and use thereof. In particular, the present invention relates to a novel protease having a high activity under high temperature and high alkaline conditions, and a pro-form thereof, a polynucleotide encoding the protease or the pro-form, and use of the protease, the pro-form or the polynucleotide.

BACKGROUND ART

Protease is a collective term for enzymes catalyzing hydrolysis of peptide bonds and is present ubiquitously in microorganisms, animals and plants. A protease is also a typical industrial enzyme and is used extensively in the fields of detergents, leather processing, food processing and functional peptide production. Particularly, from the viewpoint of prevention of secondary infection via medical apparatus, there are few alternative solutions to protease-mediated degradation of infectious protein contaminants on medical apparatus. For practical use, the most important properties of an industrial enzyme are high stability and high activity under the conditions of use. Particularly, high physicochemical stability to heat is often required and thus heat-resistant proteases are extensively used as an industrial protease. Currently, as an industrial protease, subtilisin family proteases such as subtilisin carlsberg and Proteinase K are known. In particular, Prionzyme available from the U.S. company Genencor has the highest stability among commercial proteases and is used for apparatus cleansing which is intended to prevent transmission of abnormal prion proteins, which are causative agents of prion diseases such as CJD (Creutzfeldt-Jakob disease). However, the optimum conditions for Prionzyme are limited to a temperature of 40 to 60° C. and a pH of 8 to 10, and there has been a desire for practical application of proteases usable at higher temperature conditions. Accordingly, many attempts have been made to find a novel protease usable under high temperature and high alkaline conditions.

For example, the present inventors found a subtilisin family protease derived from a hyperthermophilic archaeon, *Thermococcus kodakaraensis* KOD1 (hereinafter referred to as "Tk-subtilisin"), and reported that Tk-subtilisin shows the highest activity at pH 9.5 at a temperature of 80 to 100° C. among various conditions and has the highest thermostability among known proteases (see nonpatent literature 1 and 2). The patent literature 1 discloses a heat-resistant protease derived from the same *Thermococcus kodakaraensis* KOD1 and reports that the optimum temperature for this heat-resistant protease is about 80° C., that the protease has such a heat resistance that the residual activities are about 75% and about 50% after 120 minute-incubation at 70° C. and 80° C., respectively, and that the protease has such an alkali resistance that the residual activities are 90% or more and about 85% after 120 minute-incubation at pH 11 and pH 11.5, respectively.

CITATION LIST

Patent Literature

Patent Literature 1: JP-A 2007-6846

Nonpatent Literature

Non Patent Literature 1:
Kannan, Y., Koga, Y., Inoue, Y., Haruki, M., Takagi, M., Imanaka, T. et al. Active subtilisin-like protease from a hyperthermophilic archaeon in a form with a putative prosequence. Appl. Environ. Microbiol. 67, 2445-2552 (2001)
Non Patent Literature 2:
Pulido, M., Saito, K., Tanaka, S., Koga, Y., Takano, K. & Kanaya, S. Ca2+-dependent maturation of Tksubtilisin from a hyperthermophilic archaeon: propeptide is a potent inhibitor of the mature domain but is not required for its folding. Appl. Environ. Microbiol. 72, 4154-4162 (2006)

SUMMARY OF INVENTION

Technical Problem

As exemplified by the protease described in the nonpatent literature 1 and 2, and the heat-resistant protease described in the patent literature 1, novel proteases usable under high temperature and high alkaline conditions have been already found, but not yet used practically. Industrial proteases are often used as an ingredient of detergents and thus need to be stable and active even in the presence of surfactants. Therefore, a major challenge in the technical field concerned is still to find a further novel protease, to clarify its function and then to put the protease into practical use as an industrial protease through research and development.

Accordingly, an object of the present invention is to provide a novel protease which has a high activity under high temperature and high alkaline conditions, a high stability to protein denaturants and surfactants and high effectiveness as a protease used in detergents.

Solution to Problem

In order to achieve the object, the present invention includes the following inventions.
[1] A protease comprising any one of the following amino acid sequences (a) to (d):
(a) the amino acid sequence of SEQ ID NO: 1,
(b) an amino acid sequence having deletion, substitution or addition of one to several amino acids in the amino acid sequence of SEQ ID NO: 1,
(c) the amino acid sequence of SEQ ID NO: 3, and
(d) an amino acid sequence having deletion, substitution or addition of one to several amino acids in the amino acid sequence of SEQ ID NO: 3.
[2] The protease according to the above [1], wherein the optimum temperature for the protease is 100° C. or higher in the case where a reaction of the protease using azocasein as a substrate is performed at pH 7 for 20 minutes.
[3] The protease according to the above [1], wherein the residual activity of the protease is 40% or more after the protease is treated in 50 mM Tris-HCl (pH 7) at 100° C. for 90 minutes.
[4] The protease according to the above [1], wherein the residual activity of the protease is 80% or more after the protease is treated in 20 mM Tris-HCl (pH 8) containing 5% sodium dodecyl sulfate at 55° C. for 60 minutes.

[5] The protease according to the above [1], wherein the Km value of the protease is 0.1 to 1 mM in the case where a reaction of the protease using Suc-AAPF-pNA as a substrate is performed at 80° C.

[6] A pro-form of the protease according to any one of the above [1] to [5], which comprises the following amino acid sequence (e) or (f):

(e) the amino acid sequence of SEQ ID NO: 5, or (f) an amino acid sequence having deletion, substitution or addition of one to several amino acids in the amino acid sequence of SEQ ID NO: 5.

[7] A polynucleotide encoding the protease according to any one of the above [1] to [5].

[8] The polynucleotide according to the above [7], which comprises the base sequence of SEQ ID NO: 2 or 4, or which encodes a protease and hybridizes to a polynucleotide comprising the complementary base sequence of SEQ ID NO: 2 or 4 under stringent conditions.

[9] A polynucleotide encoding the pro-form according to the above [6].

[10] The polynucleotide according to the above [9], which comprises the base sequence of SEQ ID NO: 6, or which encodes a pro-form and hybridizes to a polynucleotide comprising the complementary base sequence of SEQ ID NO: 6 under stringent conditions.

[11] An expression vector comprising the polynucleotide according to any one of the above [7] to [10].

[12] A transformant having the expression vector according to the above [11] transferred thereinto.

[13] An antibody which specifically binds to the protease according to any one of the above [1] to [5].

[14] A detergent comprising the protease according to any one of the above [1] to [5].

Advantageous Effects of Invention

The present invention can provide a protease which, in comparison with conventional ones, has a higher activity under high temperature and high alkaline conditions, a higher stability to protein denaturants and surfactants, and the capability of degrading a low concentration of substrates. This protease is greatly useful as a protease that can be blended into any of various detergents for use under high temperature and high alkaline conditions.

DESCRIPTION OF EMBODIMENTS

Figure 1:
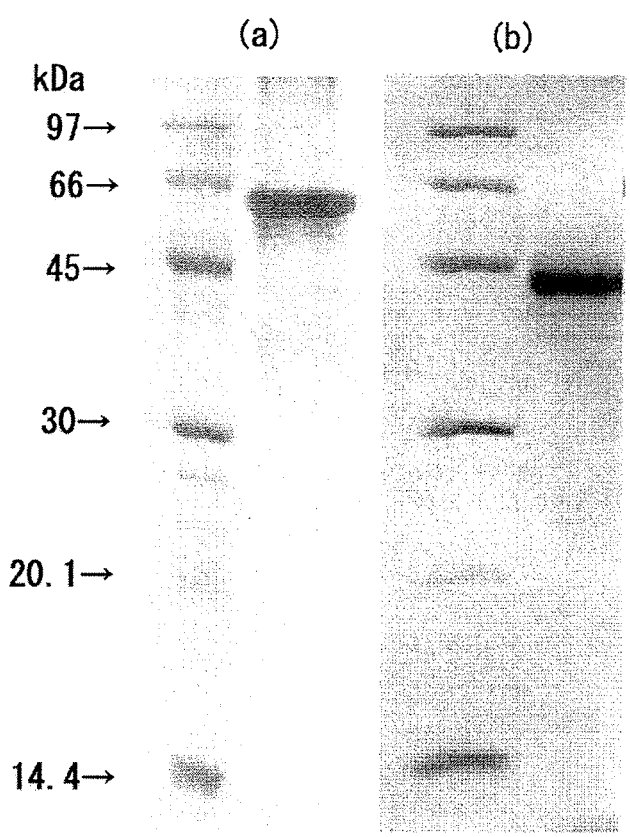
FIG. 1(a) is an image showing the SDS-PAGE results of the pro-form of the present invention (proTk-SP).
FIG. 1(b) is an image showing the SDS-PAGE results of the protease of the present invention obtained by incubation of the proTk-SP at 80° C. for 120 minutes.

Protease and its Pro-Form (1) Preparation of Protease

The protease of the present invention is a novel protease derived from a hyperthermophilic archaeon, *Thermococcus kodakaraensis* KOD1 (Morikawa M et al. Appl Environ Microbiol, 1994 December; 60 (12): 4559-66, hereinafter referred to as KOD1). KOD1 was deposited with the independent administrative institution RIKEN BioResource Center under the accession number JCM12380. The complete genome of KOD1 was already decoded, in which 2036 protein coding regions (CDSs) were identified and about half of them (1165 CDSs) were annotated (Fukui T et al., Genome Res, 2005 March; 15 (3): 352-63). The 2088737-bp complete genome sequence of KOD1 was registered with DDBJ/EMBL/GenBank under the accession number AP006878.

Based on the genomic information on KOD1, the present inventors focused their attention to the base sequence predicted to encode a subtilisin-like serine protease precursor (ACCESSION: AP006878 REGION: 1484233 ... 1486224, SEQ ID NO: 8), and identified a specified partial sequence of the full length protein encoded by the base sequence as the one which constitutes a mature protein having protease activity. Generally, proteases of the subtilisin family have a long pre-pro sequence. It is said that the proteases require a pre-sequence (also called a signal sequence) for their exocytic release and a pro-sequence for formation of their active conformation. Then, based on the base sequence (SEQ ID NO: 8), the present inventors amplified DNA of the region predicted to encode the protease precursor (pro-form), which has the pro-sequence and the mature sequence but excludes the pre-sequence (signal sequence). The present inventors inserted the resulting DNA fragment into an expression vector and transferred the expression vector into *Escherichia coli* for expression of the objective protein (pro-form). By incubating the resulting pro-form for processing (maturation), for example at pH 9 at 80° C. for 120 minutes, the present inventors obtained a mature protein having protease activity, i.e. the protease of the present invention.

The protease of the present invention comprises any one of the following amino acid sequences (a) to (d).
(a) The amino acid sequence of SEQ ID NO: 1
(b) An amino acid sequence having deletion, substitution or addition of one to several amino acids in the amino acid sequence of SEQ ID NO: 1
(c) The amino acid sequence of SEQ ID NO: 3
(d) An amino acid sequence having deletion, substitution or addition of one to several amino acids in the amino acid sequence of SEQ ID NO: 3

The amino acid sequence of SEQ ID NO: 1 corresponds to the region from residue 137 to residue 562 of the amino acid sequence (ACCESSION: BAD85878, SEQ ID NO: 7) deduced from the base sequence predicted to encode the above-mentioned subtilisin-like serine protease precursor (ACCESSION: AP006878 REGION: 1484233 ... 1486224, SEQ ID NO: 8). The amino acid sequence of SEQ ID NO: 3 corresponds to the region from residue 137 to residue 563 of the amino acid sequence (SEQ ID NO: 7) deduced from the base sequence predicted to encode the above-mentioned subtilisin-like serine protease precursor (SEQ ID NO: 8).

The pro-form of the present invention is a pro-form of the protease of the present invention and comprises the following amino acid sequence (e) or (f).
(e) The amino acid sequence of SEQ ID NO: 5
(f) An amino acid sequence having deletion, substitution or addition of one to several amino acids in the amino acid sequence of SEQ ID NO: 5

As used herein, the term "pro-form" refers to a protease precursor which has a pro-sequence and a mature sequence but no pre-sequences.

The amino acid sequence of SEQ ID NO: 5 corresponds to the region from residue 24 to residue 663 of the amino acid sequence (SEQ ID NO: 7) deduced from the base sequence predicted to encode the above-mentioned subtilisin-like serine protease precursor (SEQ ID NO: 8). The one which excludes the region of residue 1 to residue 113 and the region of residue 540 to residue 640 from the amino acid sequence of the pro-form (SEQ ID NO: 5) is a protease comprising the amino acid sequence of SEQ ID NO: 1. The one which excludes the region of residue 1 to residue 113 and the region of residue 541 to residue 640 from the amino acid sequence of the pro-form (SEQ ID NO: 5) is a protease comprising the amino acid sequence of SEQ ID NO: 3.

As used herein, "having deletion, substitution or addition of one to several amino acids" means having deletion, substitution or addition of an amino acid(s), the number of which is in the range allowed by a known preparation method for mutant peptides, such as site-directed mutagenesis (preferably 10 or less, more preferably 7 or less, and even more preferably 5 or less). Such a mutant protein is not limited to a protein artificially mutated by a known preparation method for mutant polypeptides, and may be a protein isolated and purified from nature. It is well known in the art that modification to some amino acids in the amino acid sequence of a protein can be easily made without any significant effect on the structure or function of the protein. In addition to such artificial modification, it is also well known that there are natural mutants having no significant changes in the structure or function in comparison with wild-type proteins.

A preferable mutant has a conservative or non-conservative amino acid substitution, deletion or addition. More preferably, the mutant has a silent substitution, deletion or addition, and particularly preferably a conservative substitution, none of which alter the polypeptide activity of the present invention. Typical examples of the conservative substitution include substitution whereby one amino acid is exchanged for another among aliphatic amino acids Ala, Val, Leu and Ile, exchange between hydroxyl residues Ser and Thr, exchange between acidic residues Asp and Glu, substitution between amide residues Asn and Gln, exchange between basic residues Lys and Arg, and substitution between aromatic residues Phe and Tyr.

The protease and the pro-form of the present invention may contain an additional peptide. Examples of the additional peptide include epitope peptides for labelling, such as a polyhistidine tag (His-tag), Myc and FLAG.

The protease and the pro-form of the present invention can be prepared by (I) culturing bacteria which produce the protease of the present invention and then conducting isolation and purification of the protease or the pro-form. The protease and the pro-form can be also prepared by (II) a known genetic engineering technique, specifically, by isolating a gene encoding the protease or pro-form of the present invention from bacteria, constructing a recombinant expression vector and then transferring the vector into an appropriate host cell for expression of a recombinant protein. Alternatively, the protease and the pro-form can be prepared by (III) in vitro coupled transcription-translation system. Bacteria that can be used for preparation of the protease of the present invention are not particularly limited as long as they can produce the protease of the present invention. Preferable examples of the bacteria include KOD1 described above.

In the case where the above method (I) is employed with KOD1, culture of KOD1 can be performed under the culture conditions described in Morikawa. et al. Appl. Environ. Microbiol. 60: 4559-4566. (1994), for example. After several days of the culture, the KOD1 cells are removed from the culture medium and the protease or the pro-form is separated and purified from the remaining culture medium by a known technique, specifically including separation techniques such as salting-out, precipitation and ultrafiltration; purification techniques such as ion exchange chromatography, isoelectric chromatography, hydrophobic chromatography, gel filtration chromatography, adsorption chromatography, affinity chromatography and reversed phase chromatography; and a combination of the foregoing techniques.

The above method (II) will be described in detail in the sections below of [polynucleotide], [expression vector] and [transformant].

In the case where the above method (III) is employed, a DNA fragment encoding the protease or pro-form of the present invention can be used with a known in vitro coupled transcription-translation system (for example, a system using cell-free extract of *Escherichia coli*, wheat germ cells or rabbit retinal cells).

Identification of the thus obtained protease or pro-form can be performed using a known method. For example, the obtained protease is separated by polyacrylamide gel electrophoresis and then transferred to a polyvinylidene fluoride (PVDF) membrane, and after Coomassie Brilliant Blue staining, the band of the objective protein is excised from the stained membrane. Using tryptic digest of the band, peptide mass fingerprinting can be performed by MALDI-TOF MS for protein identification. Also, amino acid sequence determination can be performed, for example, using an automated peptide sequencer.

(2) Biochemical Properties of Protease
(i) Optimum pH (See Example 2)

In the case where the protease of the present invention is incubated with Suc-AAPF-pNA serving as a substrate at 20° C. for 10 minutes, the optimum pH ranges at least from 6 to 11.5, and it is expected that the high activity is maintained even above pH 11.5. Thus, the protease of the present invention is suitable for use in diverse pH environments at pH 6 or above.

(ii) Optimum Temperature (See Example 3)

In the case where the reaction of the protease using azocasein as a substrate is performed at pH 7 for 20 minutes, the optimum temperature is 100° C. or higher. Thus, the protease of the present invention is suitable for use in high temperature environments, and for example, when blended into detergents for medical apparatus which are intended for degradation of infectious protein contaminants, the protease can be expected to provide an excellent effect.

(iii) Thermostability (See Example 4)

After the protease is treated in a solution at 100° C. for 90 minutes, the residual activity is 40% or more. After the protease is treated in a solution at 90° C. for 180 minutes, the residual activity is 80% or more. After the protease is treated at 80° C. for 180 minutes, the activity of the protease remains unchanged from that before the heat treatment. Thus, the protease of the present invention, which has an extremely high thermostability, is suitable for use in high temperature environments.

(iv) Stability to Protein Denaturants, Surfactants and Chelating Agents (See Example 5)

After the protease is treated in 20 mM Tris-HCl (pH 8) containing 8 M urea at 55° C. for 60 minutes, the residual activity is 80% or more.

After the protease is treated in 20 mM Tris-HCl (pH 8) containing 2 M guanidine hydrochloride at 55° C. for 60 minutes, the residual activity is 60% or more.

After the protease is treated in 20 mM Tris-HCl (pH 8) containing 10% Triton X-100 at 55° C. for 60 minutes, the residual activity is 95% or more.

After the protease is treated in 20 mM Tris-HCl (pH 8) containing 10% Tween 20 at 55° C. for 60 minutes, the residual activity is 95% or more.

After the protease is treated in 20 mM Tris-HCl (pH 8) containing 5% sodium dodecyl sulfate at 55° C. for 60 minutes, the residual activity is 80% or more.

After the protease is treated in 20 mM Tris-HCl (pH 8) containing 10 mM EDTA at 55° C. for 60 minutes, the activity of the protease remains unchanged from that before the treatment.

Thus, the protease of the present invention, which has a high stability to various kinds of protein denaturants, surfactants and chelating agents, is advantageous in that the protease can be blended into a composition containing a protein denaturant, a surfactant and/or a chelating agent and also used as an industrial protease in a wide range of applications.

(v) Km Value (See Example 7)

In the case where the reaction of the protease using Suc-AAPF-pNA as a substrate is performed at 80° C., the Km value is 0.1 to 1 mM. This value is about 1/10 of the Km value of the above-mentioned Tk-subtilisin (see nonpatent literature 1 and 2), suggesting that, in comparison with Tk-subtilisin, the protease of the present invention can more efficiently degrade a low concentration of the substrate. Thus, the protease of the present invention can be preferably used in various applications including detergents for medical apparatus (infectious protein contaminants on medical apparatus may cause secondary infection).

(vi) Calcium Ion Non-Requirement for Structure Formation (See Example 8)

The protease of the present invention does not require calcium ions for structure formation and can exert a stable protease activity even in the absence of calcium ions.

This is one of the characteristics of the protease of the present invention in contrast to Tk-subtilisin, a protease derived from the same *Thermococcus kodakaraensis* KOD1, which shows an extremely strong calcium requirement. Thus, the protease of the present invention has an extremely excellent advantage that it can exert a stable activity, for example, even in a detergent containing a chelating agent as an additive.

The activity of the protease of the present invention can be determined in accordance with the descriptions in the Examples below. To be more specific, the protease is allowed to hydrolyze peptide bonds in a substrate such as Suc-AAPF-pNA and azocasein and the chromogen released from the substrate is quantified based on the absorbance. In this way, the amount of the peptide bond cleaved by the enzyme can be calculated, and thus the enzyme activity can be determined.

[Polynucleotide]

The polynucleotide of the present invention encodes the protease of the present invention. Specific examples thereof include the following polynucleotides (A) to (D).

(A) a polynucleotide encoding a protease comprising the amino acid sequence of SEQ ID NO: 1

(B) a polynucleotide encoding a protease comprising an amino acid sequence having deletion, substitution or addition of one to several amino acids in the amino acid sequence of SEQ ID NO: 1

(C) a polynucleotide encoding a protease comprising the amino acid sequence of SEQ ID NO: 3

(D) a polynucleotide encoding a protease comprising an amino acid sequence having deletion, substitution or addition of one to several amino acids in the amino acid sequence of SEQ ID NO: 3

In another aspect of the present invention, the polynucleotide encodes the pro-form of the present invention. Specific examples thereof include the following polynucleotides (E) and (F).

(E) a polynucleotide encoding a pro-form comprising the amino acid sequence of SEQ ID NO: 5

(F) a polynucleotide encoding a pro-form comprising an amino acid sequence having deletion, substitution or addition of one to several amino acids in the amino acid sequence of SEQ ID NO: 5

As used herein, the term "polynucleotide" is interchangeable with the term "gene", "nucleic acid" or "nucleic acid molecule". The polynucleotide of the present invention can be present in the form of RNA (for example, mRNA) or DNA (for example, cDNA or genomic DNA). DNA may be a double strand or a single strand. A single-stranded DNA or RNA may be a coding strand (sense strand) or a non-coding strand (antisense strand). The polynucleotide of the present invention may be fused with a polynucleotide encoding a tag for labelling (a tag sequence or a marker sequence) at the 5'- or 3'-terminus.

Preferably, the polynucleotide encoding the protease of the present invention is a polynucleotide comprising the base sequence of SEQ ID NO: 2 or 4, or a polynucleotide which encodes a protease and hybridizes to a polynucleotide comprising the complementary base sequence of SEQ ID NO: 2 or 4 under stringent conditions.

Preferably, the polynucleotide encoding the pro-form of the present invention is a polynucleotide comprising the base sequence of SEQ ID NO: 6, or a polynucleotide which encodes a pro-form and hybridizes to a polynucleotide comprising the complementary base sequence of SEQ ID NO: 6 under stringent conditions.

The base sequence of SEQ ID NO: 2 corresponds to the region from position 409 to position 1686 of the base sequence predicted to encode the above-mentioned subtilisin-like serine protease precursor (ACCESSION: AP006878 REGION: 1484233 . . . 1486224, SEQ ID NO: 8), and the base sequence of SEQ ID NO: 4 corresponds to the region from position 409 to position 1689 of SEQ ID NO: 8. The base sequence of SEQ ID NO: 6 corresponds to the region from position 70 to position 1992 of SEQ ID NO: 8.

Hybridization can be performed according to a well-known method as described in Sambrook et al., Molecular Cloning, A Laboratory Manual, 3rd Ed., Cold Spring Harbor Laboratory (2001). Usually, as the temperature becomes higher and the salt concentration becomes lower, the conditions of hybridization become more stringent (this means that hybridization becomes harder to achieve), and thereby more homologous polynucleotides can be obtained. A suitable hybridization temperature varies with the base sequence and the length thereof, and for example, in the case where an 18-base DNA fragment encoding 6 amino acids is used as a probe, the temperature is preferably 50° C. or lower.

The procedure for "hybridizes under stringent conditions" means that the filter is incubated in a hybridization solution (50% formamide, 5×SSC (150 mM NaCl and 15 mM trisodium citrate), 50 mM sodium phosphate (pH 7.6), 5×Denhardt's solution, 10% dextran sulfate and 20 µg/ml denatured sheared salmon sperm DNA) at 42° C. overnight and then washed in 0.1×SSC at about 65° C.

Preferably, the polynucleotide of the present invention encodes a protease and comprises a base sequence having at least 80% homology, more preferably at least 85%, 90%, 92%, 95%, 96%, 97%, 98% or 99% homology to the complementary base sequence of SEQ ID NO: 2 or 4. Preferably, the polynucleotide of the present invention encodes a pro-form and comprises a base sequence having at least 80% homology, more preferably at least 85%, 90%, 92%, 95%, 96%, 97%, 98% or 99% homology to the complementary base sequence of SEQ ID NO: 6.

Whether a certain polynucleotide is, for example, at least 80%, 85%, 90%, 92%, 95%, 96%, 97%, 98% or 99% homologous to the base sequence of SEQ ID NO: 2 can be confirmed by a known computer program (for example, Bestfit program (Wisconsin Sequence Analysis Package, Version 8 for Unix (registered trademark)), Genetics Computer Group, University Research Park, 575 Science Drive, Madison, Wis. 53711).

The polynucleotide of the present invention encompasses, in addition to a double-stranded DNA, a single-stranded DNA or RNA which is a sense or antisense strand constituting a double-stranded DNA. The polynucleotide of the present invention may contain an untranslated region (UTR) sequence, a vector sequence (including an expression vector sequence), etc.

Examples of the method for obtaining the polynucleotide of the present invention include a method using amplification technique such as PCR. For example, based on the 5'- and 3'-terminal sequences of the base sequence of SEQ ID NO: 2 (or their complementary sequences), respective primers are designed, and using these primers and using genomic DNA, cDNA or the like as a template, PCR or the like is conducted to amplify a DNA region flanked by both primers. In this way, a DNA fragment containing the polynucleotide of the present invention can be obtained in a large amount.

[Expression Vector]

The present invention provides an expression vector used for preparation of the protease of the present invention. The expression vector of the present invention is not particularly limited as long as it contains the above-described polynucleotide encoding the polypeptide of the present invention, and for example, plasmid vectors carrying a recognition sequence for RNA polymerase (pSP64, pBluescript, etc.) are preferred. The preparation method for recombinant expression vectors is not particularly limited, and examples thereof include methods using a plasmid, a phage or a cosmid. The kind of the vector is not particularly limited, and a vector that can be expressed in host cells can be appropriately selected. To be more specific, depending on the kind of the host cell, a promoter sequence to ensure the expression of the polynucleotide of the present invention is appropriately selected, and this promoter sequence and the polynucleotide of the present invention are inserted into any of various plasmids etc. for preparation of the expression vector of the present invention.

After a host transformed with the expression vector of the present invention is cultured, cultivated or bred, the protease or pro-form of the present invention can be collected and purified from the cultures etc. according to conventional methods (for example, filtration, centrifugation, cell disruption, gel filtration chromatography, ion exchange chromatography, etc.).

The expression vector preferably contains at least one selection marker. Examples of such a marker include a dihydrofolate reductase gene and a neomycin resistance gene for eukaryotic cell culture; and a tetracycline resistance gene and an ampicillin resistance gene for culture of E. coli and other bacteria. By use of such a selection marker, it can be confirmed whether the polynucleotide of the present invention has been transferred into host cells and then expressed therein without fail. Also, the polypeptide of the present invention may be expressed as a fusion polypeptide. For example, by use of green fluorescent protein (GFP) derived from Aequorea coerulescens as a marker, the polypeptide of the present invention may be expressed as a GFP fusion polypeptide.

The host cell described above is not particularly limited, and various known cells can be preferably used. Specific examples of the host cell include bacteria such as Escherichia coli, yeasts (budding yeast Saccharomyces cerevisiae and fission yeast Schizosaccharomyces pombe), nematodes (Caenorhabditis elegans), Xenopus laevis oocytes and animal cells (for example, CHO cells, COS cells and Bowes melanoma cells). The method for transferring the expression vector described above into host cells, i.e., the transformation method, is not particularly limited, and known methods such as electroporation, the calcium phosphate method, the liposome method and the DEAE dextran method can be used preferably.

[Transformant]

The present invention provides a transformant having the expression vector of the present invention transferred thereinto. As used herein, the term "transformant" encompasses a cell, a tissue and an organ as well as an individual organism. The organism to be transformed is not particularly limited, and examples thereof include various microorganisms, plants and animals mentioned as examples of the host cell described above.

The transformant of the present invention is characterized by expressing the protease or pro-form of the present invention. It is preferable that the transformant of the present invention stably expresses the protease or pro-form of the present invention, but the transformant may transiently express the same.

[Antibody]

The present invention provides an antibody which specifically binds to the protease of the present invention. The antibody of the present invention is preferably an antibody which binds to the protease of the present invention, but not to the precursor thereof. The antibody of the present invention can be used for detection and separation of the protease of the present invention.

As used herein, the term "antibody" refers to an immunoglobulin (IgA, IgD, IgE, IgG, IgM and their fragments (a Fab fragment, a F(ab')2 fragment, an Fc fragment, etc.)), and examples of the antibody include, but are not limited to, a polyclonal antibody, a monoclonal antibody and a single-chain antibody. The antibody can be prepared according to any of various known methods (for example, Harlow at al., "Antibodies: a laboratory manual", Cold Spring Harbor Laboratory, New York (1988); and Iwasaki at al., "Monoclonal antibody, hybridoma and ELISA", Kodansha Ltd. (1991)).

[Application of Protease]

The protease of the present invention, which has a higher activity under high temperature and high alkaline conditions as well as a higher stability to protein denaturants and surfactants in comparison with known industrial proteases, can be blended into detergents for use at a high temperature in order to strengthen their detergency. Further, since the protease of the present invention can degrade a low concentration of substrates, it has high effectiveness for degradation and cleansing of infectious protein contaminants on medical apparatus, which may cause secondary infection. That is, the protease of the present invention can be preferably used for various detergents, such as detergents for medical apparatus, dishwasher detergents and laundry detergents. Also, the protease of the present invention can be used for, in addition to such detergents, feed processing, food processing (fish oil processing, meat processing, etc.), textile processing, wool processing, leather processing, contact lens cleansing, pipe cleaning, etc., and also may be blended into bath salts and depilatories. Further, the protease of the present invention can be used as a protease for sample pretreatment in the preparation of nucleic acids, such as DNA, from tissues and cells.

The present invention provides a detergent (a composition for cleansing) containing the protease of the present invention. The protease content in the detergent is not particularly limited, but because of high activity and high stability to surfactants, even a small amount of the protease can provide a detergent with high detergency. A preferable protease content is, for example, 0.1 to 10% by weight. Too low a protease content cannot provide a sufficient cleansing effect, and conversely, too high a protease content cannot provide an improved cleansing effect proportional to the content, leading to economical inefficiency. The protease of the present invention can be blended into any known detergent without any alteration of the composition of the detergent. There is no particular limitation on the ingredient of the detergent containing the protease of the present invention. A typical example of such a detergent is a detergent containing 10 to 50% by weight of a surfactant, 0 to 50% by weight of a builder, 1 to 50% by weight of an alkaline agent or an inorganic electrolyte, 0.1 to 5% by weight of one or more kinds of ingredients selected from the group consisting of an anti-redeposition agent, an enzyme, a bleaching agent, a fluorescent dye, an anti-caking agent and an antioxidant, relative to the weight of the detergent.

EXAMPLES

Hereinafter, the present invention will be illustrated in more detail by Examples, but is not limited thereto. In the following Examples, the protease of the present invention is called "Tk-SP" and the pro-form thereof is called "proTk-SP" in some cases.

Example 1

Preparation of Novel Protease (Tk-SP)

1-1. Expression and Purification of Pro-Form (proTk-SP)

Based on the genomic information on *Thermococcus Kodakaraensis* KOD1 (ACCESSION: AP006878), for expression of a pro-form which excludes the putative signal sequence (pre-sequence) from the deduced amino acid sequence (ACCESSION: BAD85878, SEQ ID NO: 7) of the base sequence predicted to encode a subtilisin-like serine protease precursor (ACCESSION: AP006878 REGION: 1484233 . . . 1486224, SEQ ID NO: 8), and contains the putative pro-sequence and mature sequence, a primer pair for amplification of a DNA fragment predicted to encode the pro-form was designed. The primer pair consists of a forward primer having an NdeI site (5'-GGCCTTTATCATATGGC-CCCCCAGAAG-3' (SEQ ID NO: 9)) and a reverse primer having a BamHI site (5'-GGCCTTGGATCCTCACCCG-TAGTAAAC-3' (SEQ ID NO: 10)). Using the primer pair and using the genomic DNA of KOD1 as a template, PCR was performed to amplify the DNA fragment. Digestion of the resulting DNA fragment by NdeI and BamHI gave a 1.9-kb DNA fragment, this fragment was ligated into the NdeI/BamHI site of pET25b (manufactured by Novagen), and thus pET25b-proTk-SP was constructed. With this plasmid (pET25b-proTk-SP), *Escherichia coli* BL21 (DE3) Codon-Plus was transformed into a strain which massively expresses the proTk-SP.

The strain was cultured at 37° C. in a LB culture medium supplemented with 50 μg/ml ampicillin and 34 μg/ml chloramphenicol. When the $OD_{600}$ value reached 0.8, IPTG was added to the final concentration of 1 mM, and the culture was continued for additional 4 hours. The strain was harvested, suspended in 20 mM Tris-HCl (pH 9.0), sonicated and then centrifuged (30,000×g, 30 min). To the supernatant, 30% ammonium sulfate was added and the resulting precipitate was collected by centrifugation (30,000×g, 30 min). This precipitate was dissolved in 20 mM Tris-HCl (pH 7.0) and the solution was dialyzed against 20 mM Tris-HCl (pH 7.0) for removal of ammonium sulfate. Using the supernatant obtained after the dialysis, purification was performed with the anion exchange column Hitrap Q (manufactured by GE Healthcare).

1-2. Preparation, Molecular Weight Analysis and N-Terminal Analysis of Mature Protein (Tk-SP)

(i) Confirmation of Processing by SDS-PAGE

The purified proTk-SP was dissolved in 1 ml of 50 mM Tris-HCl (pH 9.0) so that the protein concentration was 0.013 mg/ml, and the protein solution was incubated at 80° C. for 120 minutes. After precipitation with TCA, the resulting precipitate was subjected to 15% SDS-PAGE. The results are shown in FIGS. 1(*a*) and (*b*). (a) is an image showing the SDS-PAGE results of the proTk-SP before incubation at 80° C. for 120 minutes, and (b) is an image showing the SDS-PAGE results after incubation of the proTk-SP at 80° C. for 120 minutes. In (a), the band of the proTk-SP was observed near the position of 68.6 kDa, which is the theoretical molecular weight of its predicted amino acid sequence (SEQ ID NO: 5). In (b), the band, which was obtained by incubation of the proTk-SP at 80° C. for 120 minutes, was located at a position of about 44 kDa. The results show that the proTk-SP was processed by the incubation at 80° C. for 120 minutes.

(ii) Molecular Weight Analysis by MALDI-TOF MS

Figures 2, 3:
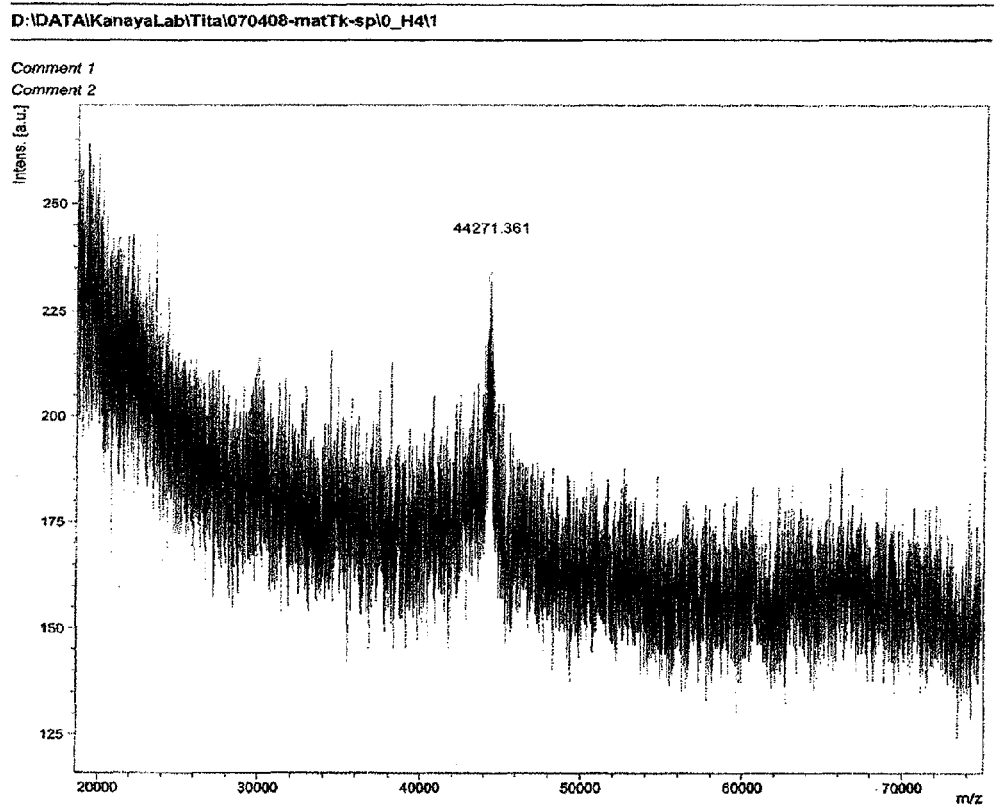
FIG. 2 is a chart showing the results of the molecular weight analysis of the protease of the present invention (Tk-SP) by MALDI-TOF MS.
FIG. 3 is a figure showing the results of the N-terminal analysis of the protease of the present invention (Tk-SP).

The purified proTk-SP was dissolved in 50 mM Tris-HCl (pH 9.0) so that the protein concentration was 1 mg/ml, and the protein solution was incubated at 80° C. for 120 minutes. After the incubation, 1 μl of the protein solution was mixed with 1 μl of a matrix solution (10 mg sinapinic acid in 1 ml of 0.1% TFA and acetonitrile in a volume ratio 2:1), and 1 μl of the mixture was used as a sample for MALDI-TOF MS (manufactured by Bruker Daltonics). The protein standard II was used as a calibration standard. The chart of MALDI-TOF MS is shown in FIG. 2. As is clear from FIG. 2, the molecular weight of this protein was 44271 Da.

(iii) N-Terminal Analysis

The processed protein (10 μg) was subjected to 15% SDS-PAGE, and after this, the protein on the gel was transferred to a PVDF membrane by blotting. From the PVDF membrane, a portion to which the objective band was transferred was excised and then subjected to N-terminal analysis by a protein sequencer (Procise automated sequencer, ABI model 491). The results are shown in FIG. 3. As shown in FIG. 3, the N-terminal amino acid sequence of this protein was VETE.

From the results of the N-terminal analysis and the molecular weight analysis, the processed protein was considered as a protein comprising the amino acid sequence of residue 114 to residue 539 of SEQ ID NO: 5 (SEQ ID NO: 1, theoretical molecular weight: 44207 Da), or a protein comprising the amino acid sequence of residue 114 to residue 540 of SEQ ID NO: 5 (SEQ ID NO: 3, theoretical molecular weight: 44322 Da). The obtained protein (Tk-SP) with a molecular weight of about 44 kDa was used for the following experiments.

Example 2 pH Dependence and Buffer Dependence of Tk-SP

For examination of the pH dependence and the buffer dependence of the Tk-SP, enzyme reactions were performed using acetate buffers (pH 4.5, 5.0, 5.2, 5.4 and 5.6), MES buffers (pH 5.5, 6.0, 6.5 and 7.0), HEPES buffers (pH 7.0 and 7.5), Tris-HCl buffers (pH 7.0, 7.5, 8.0, 8.5 and 9.0), glycine-NaOH buffers (pH 8.5, 9.0, 9.5 and 10.0) and CAPS-NaOH buffers (pH 9.0, 9.5, 10.0, 10.5, 11.0 and 11.5) in the following procedure. 100 μl of a reaction mixture containing a 50 mM buffer and 2 mM Suc-AAPF-pNA (synthetic substrate) was incubated at 20° C. for 5 minutes. To this, 0.1 μg of the Tk-SP was added and the reaction mixture was further incubated at 20° C. for 10 minutes. The reaction was stopped by addition of 10 μl of acetic acid, and then the amount of p-nitroaniline produced from the synthetic substrate Suc-AAPF-pNA was determined by use of the absorption coefficient of 8900 $M^{-1}$ $cm^{-1}$ from the absorbance at 410 nm in an ultraviolet spectrophotometer (Beckman model DU640). The amount of the enzyme which catalyzes the production of 1 μmol of p-nitroaniline per minute was defined as "one unit." The enzyme activity per milligram of the protein was defined as specific activity.

Figure 4:
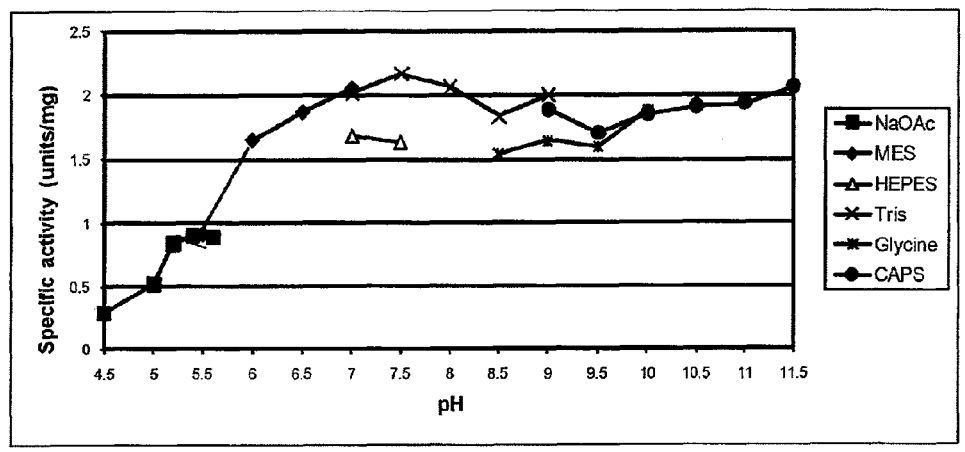
FIG. 4 is a graph showing the examination results on the pH dependence and buffer dependence of the protease of the present invention (Tk-SP).

The results are shown in FIG. 4. As shown in FIG. 4, the optimum pH for the reaction of the Tk-SP was as wide-ranging as from 6 to 11.5, and therefore, it became clear that the Tk-SP is an enzyme suitable for use in diverse pH environments at pH 6 or above.

Example 3

Temperature Dependence of Tk-SP

For examination of the temperature dependence of the Tk-SP, enzyme reactions were performed using azocasein as a substrate at various temperatures ranging from 20 to 100° C. in the following procedure. 270 μl each of a reaction mixture containing 50 mM Tris-HCl (pH 7.0) and 2% azocasein was incubated at a different temperature for 5 minutes. To each reaction mixture, 30 μl of a 3.3 μg/ml solution of the Tk-SP (about 0.1 μg) was added and the reaction mixture was further incubated for 20 minutes. The reaction was stopped by addition of 200 μl of 15% trichloroacetic acid (the final concentration of 6%). After centrifugation (15,000×g, 15 min), 160 μl of the resulting supernatant was mixed with 40 μl of 2 M NaOH and the absorbance at 440 nm ($A_{440}$) was measured. The amount of the enzyme required to increase the $A_{440}$ value of 300 μl of the reaction mixture by 1 per minute was defined as "one unit."

Figure 5:
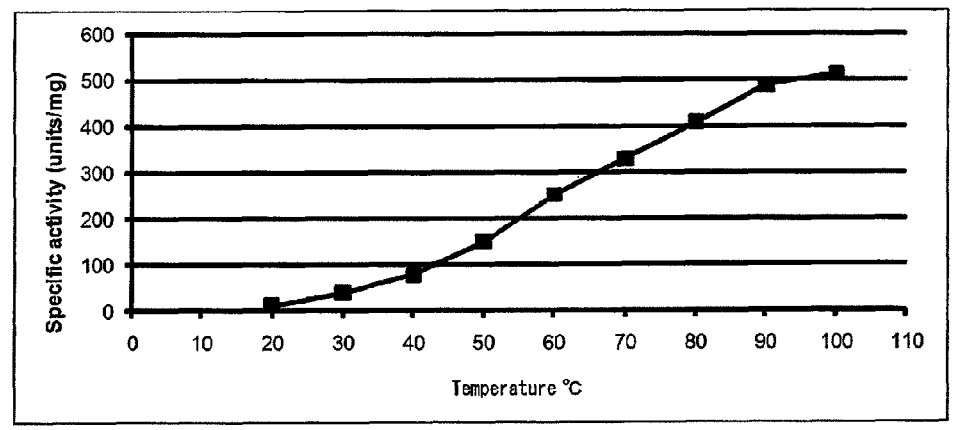
FIG. 5 is a graph showing the examination results on the temperature dependence of the protease of the present invention (Tk-SP).

The results are shown in FIG. 5. From the results shown in FIG. 5, the optimum temperature for the activity of the Tk-SP is estimated to be 100° C. or higher, and it became clear that the Tk-SP shows a high activity on peptide degradation in high temperature environments.

Example 4

Thermostability of Tk-SP

For examination of the stability of the Tk-SP against irreversible heat inactivation, a Tk-SP solution (3.3 μg/ml Tk-SP, 50 mM Tris-HCl (pH 7)) was treated at 80, 90 and 100° C. After the heat treatment, 30 μl of the Tk-SP solution and azocasein serving as a substrate were used for measurement of the residual activity at 80° C. The measurement procedure was the same as that of Example 3. The residual activity was calculated by division of the activity value after the heat treatment by the activity value before the heat treatment.

Figure 6:
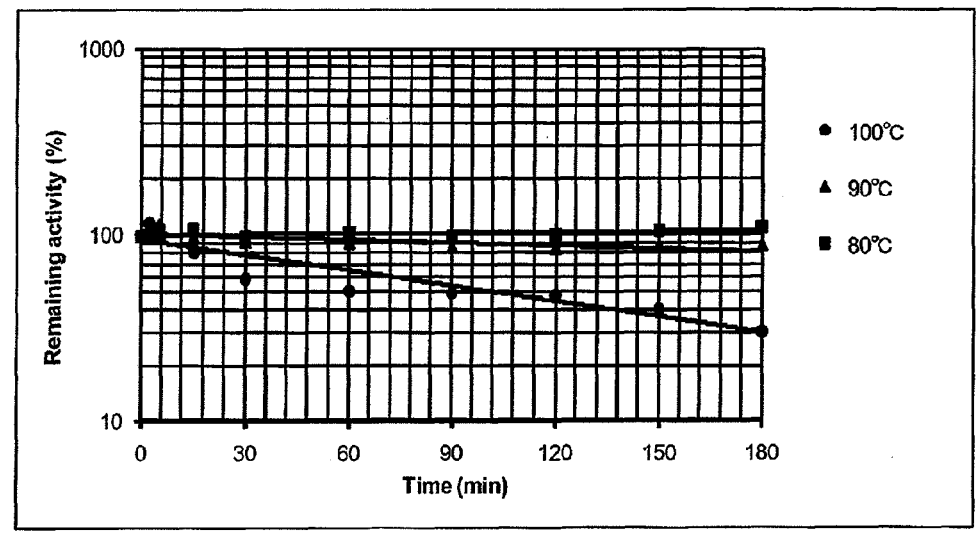
FIG. 6 is a graph showing the examination results on the thermostability of the protease of the present invention (Tk-SP).

The results are shown in FIG. 6. As is clear from FIG. 6, after treatment at 90° C. or lower for 180 minutes, the Tk-SP was not inactivated at all, and even after treatment at 100° C. for 90 minutes, half of the activity was maintained. The results clearly show that the Tk-SP has an extremely high thermostability.

Example 5

Stability of Tk-SP to Protein Denaturants, Surfactants and Chelating Agents

Urea and guanidine hydrochloride (GdnHCl) were used as a protein denaturant. Triton X-100, Tween 20 and sodium dodecyl sulfate (SDS) were used as a surfactant. EDTA was used as a chelating agent. A 0.05 mg/ml solution of the Tk-SP in 20 mM Tris-HCl (pH 8.0) was incubated with the protein denaturant, surfactant or chelating agent described above at 55° C. The concentrations of the protein denaturant and the surfactant were set at 3 to 4 levels. The concentration of EDTA was set at only one level (10 mM). The incubation time was set at 0, 2, 5, 10, 15, 30 and 60 minutes. The activity of the Tk-SP after the incubation was measured at 20° C. by use of Suc-AAPF-pNA as a substrate. The measurement procedure was the same as that of Example 2 except that the pH was 8.

Figure 7:
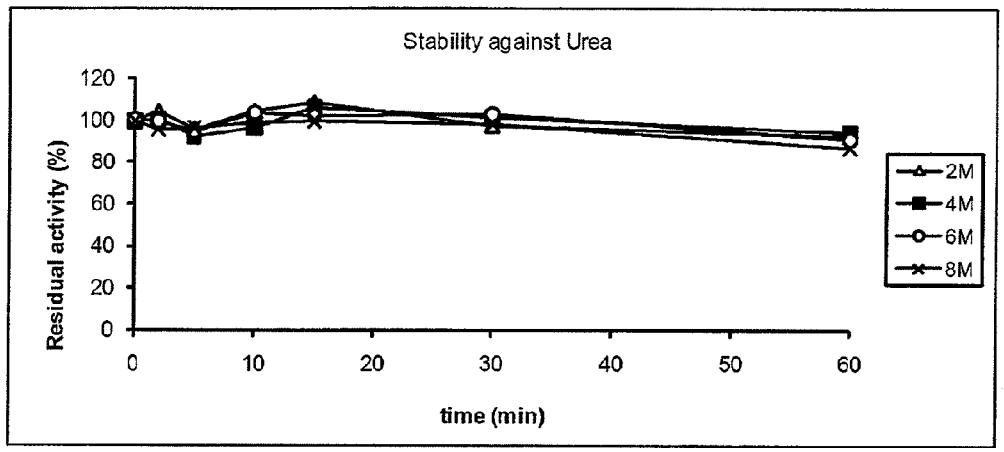
FIG. 7 is a graph showing the examination results on the stability to urea of the protease of the present invention (Tk-SP).

The results on urea are shown in FIG. 7. As is clear from FIG. 7, even after treatment with the maximum concentration (8 M) of urea for 60 minutes, the residual activity of the Tk-SP was about 90%.

Figure 8:
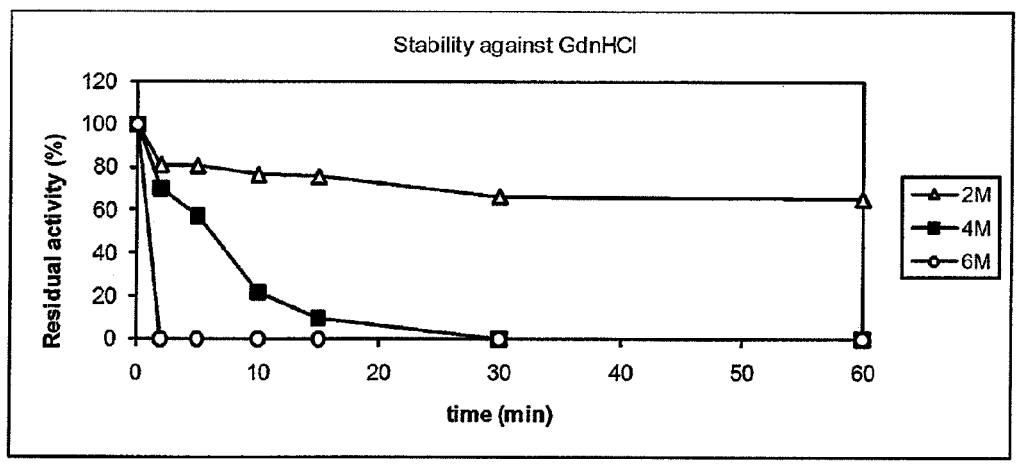
FIG. 8 is a graph showing the examination results on the stability to guanidine hydrochloride (GdnHCl) of the protease of the present invention (Tk-SP).

The results on guanidine hydrochloride (GdnHCl) are shown in FIG. 8. As is clear from FIG. 8, by treatment with 4 M GdnHCl, the Tk-SP was inactivated within 30 minutes, but after treatment with 2 M GdnHCl for 60 minutes, about 65% of the activity was maintained.

Figure 9:
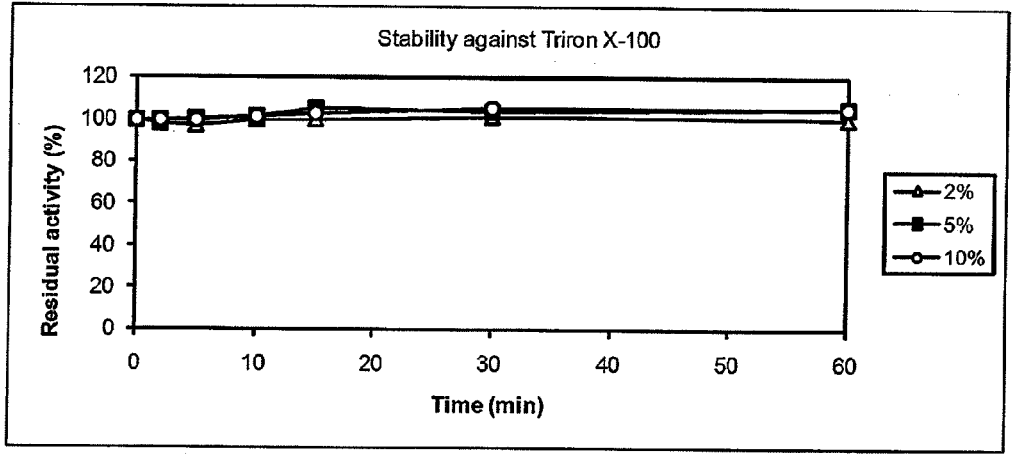
FIG. 9 is a graph showing the examination results on the stability to Triton X-100 of the protease of the present invention (Tk-SP).

The results on Triton X-100 are shown in FIG. 9. As is clear from FIG. 9, the activity of the Tk-SP remained unchanged even after treatment with the maximum concentration (10%) of Triton X-100 for 60 minutes.

Figure 10:
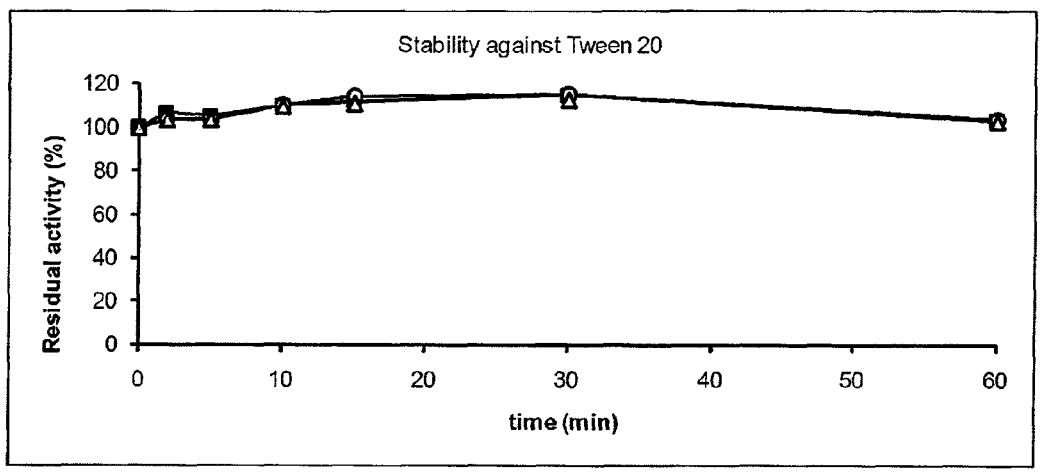
FIG. 10 is a graph showing the examination results on the stability to Tween 20 of the thermostable protease of the present invention (Tk-SP).

The results on Tween 20 are shown in FIG. 10. As is clear from FIG. 10, the activity of the Tk-SP remained unchanged even after treatment with the maximum concentration (10%) of Tween 20 for 60 minutes.

Figure 11:
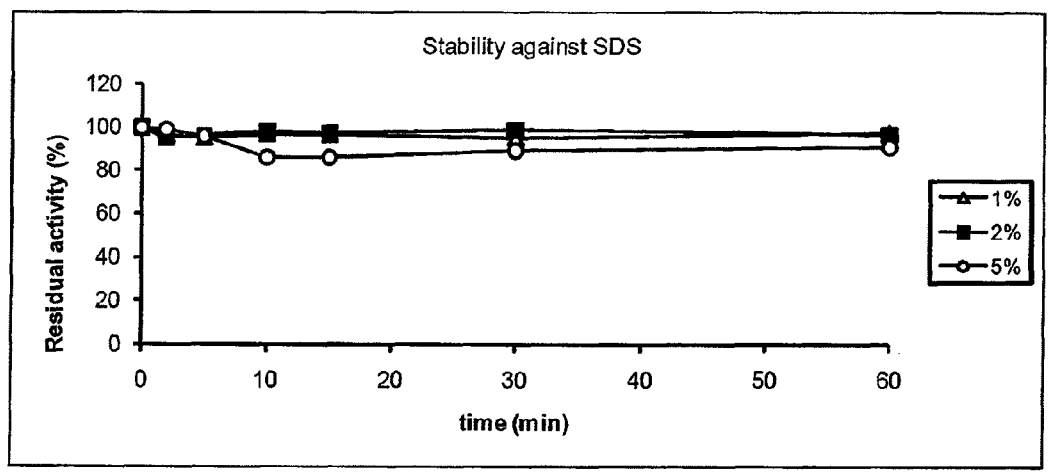
FIG. 11 is a graph showing the examination results on the stability to sodium dodecyl sulfate (SDS) of the protease of the present invention (Tk-SP).

The results on sodium dodecyl sulfate (SDS) are shown in FIG. 11. As is clear from FIG. 11, even after treatment with the maximum concentration (5%) of SDS for 60 minutes, the residual activity of the Tk-SP was about 90%.

Figure 12:
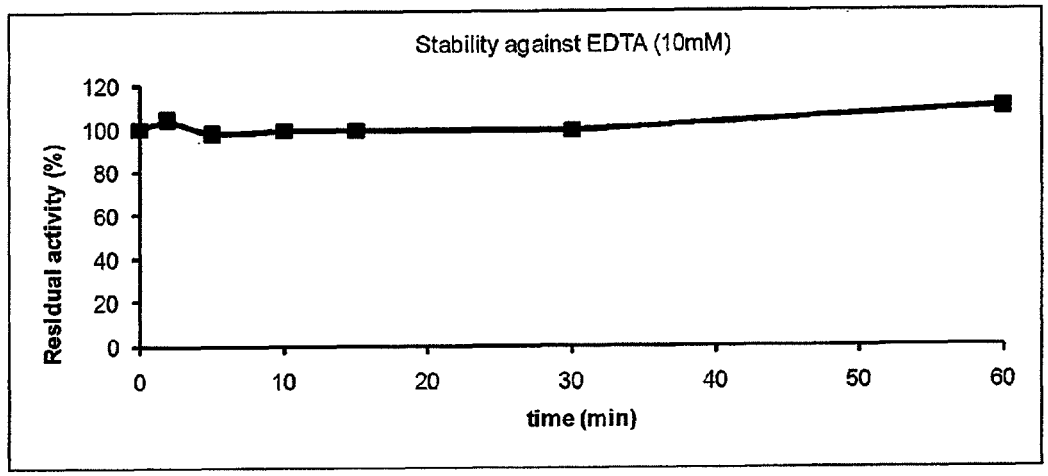
FIG. 12 is a graph showing the examination results on the stability to EDTA of the protease of the present invention (Tk-SP).

The results on EDTA are shown in FIG. 12. As is clear from FIG. 12, the activity of the Tk-SP remained unchanged even after treatment with 10 mM EDTA for 60 minutes. That is, it became clear that the Tk-SP does not require calcium ions to exert the activity.

The above results show that the Tk-SP has a high stability to various kinds of protein denaturants, surfactants and chelating agents, and thus has high effectiveness as an industrial protease.

Example 6

Effect of Calcium Ions on Stability of Tk-SP

The Tk-SP was incubated with 10 mM EDTA at 80° C. for 30 minutes, and the mixture was dialyzed against 50 mM Tris-HCl (pH 8.0) supplemented with 0.1 mM EDTA. After this, the Tk-SP solution was treated at 80, 90 and 100° C., and the stability of the Tk-SP was examined. The residual activity was measured by use of azocasein as a substrate at 80° C. The measurement procedure was the same as that of Example 3.

Figure 13:
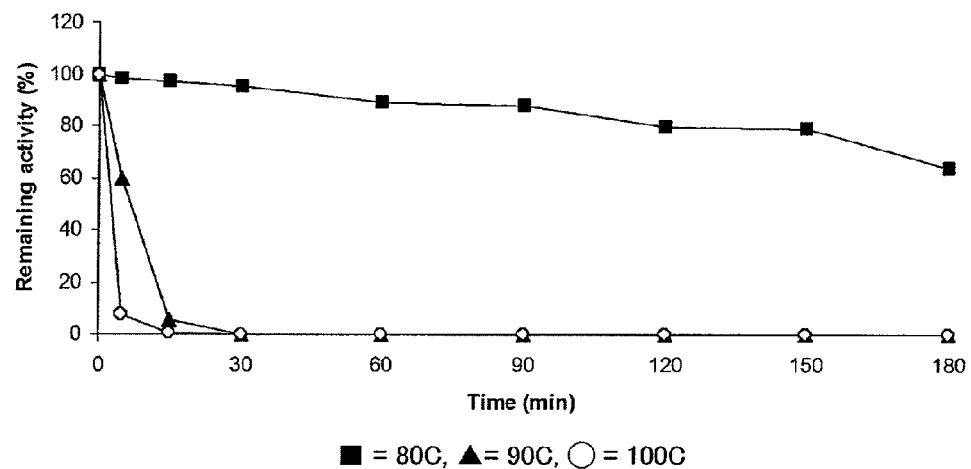
FIG. 13 is a graph showing the examination results on the effect of calcium ions on the stability of the protease of the present invention (Tk-SP).

The results are shown in FIG. 13. From the results shown in FIG. 13, it became clear that the Tk-SP shows a decreased heat resistance in the case where calcium ions are removed. This fact suggests that addition of EDTA is effective for efficient heat inactivation of the Tk-SP.

Example 7

Rate Parameters of Tk-SP

By use of, as a substrate, Suc-AAPF-pNA at various concentrations ranging from 0.01 to 2 mM, the specific activity of the Tk-SP was measured at 20 and 80° C. The measurement procedure was the same as that of Example 2. The obtained values were applied to the Michaelis-Menten equation for calculation of the rate parameters. For comparison, the specific activity of a known thermostable protease, Tk-subtilisin (see nonpatent literature 1) was similarly measured and then the rate parameters thereof were calculated.

The results are shown in Table 1. As shown in Table 1, at either temperature, the Km value of the Tk-SP was smaller than that of Tk-subtilisin (abbreviated to Tk-sub in the table). Therefore, it became clear that the Tk-SP can more efficiently degrade a low concentration of the substrate in comparison with Tk-subtilisin.

TABLE 1

| substrate | Km (mM) | | Vmax (U/mg) | | Kcat (S$^{-1}$) | |
| --- | --- | --- | --- | --- | --- | --- |
| | Tk-SP | Tk-sub | Tk-SP | Tk-sub | Tk-SP | Tk-sub |
| AAPF at 20° C. | 0.117 | 4.00 | 2.312 | 38.00 | 1.704 | 26.00 |
| AAPF at 80° C. | 0.416 | 8.00 | 34.84 | 420.00 | 25.668 | 290.00 |

Example 8

Examination of Calcium Ion Requirement for Structure Formation

A mutant which had protease activity lost by substitution of alanine for serine at residue 359 of the amino acid sequence of the proTk-SP (SEQ ID NO: 5) (hereinafter referred to as "proS359A") was used. For preparation of the proS359A, a proS359A expression vector was prepared by a known mutagenesis method from pET25b-proTk-SP constructed in Example 1, and transfer of this vector into *Escherichia coli* and expression and purification of the proS359A were conducted in the same manner as in Example 1.

Whether the proS359A formed the secondary structure was confirmed by circular dichroism measurement (CD spectrum measurement). In the measurement, the protein concentration was 0.1 mg/ml, the buffer used was 20 mM Tris-HCl (pH 7.5), and the temperature was 25° C.

It was confirmed whether the following four samples formed the secondary structure.

Sample 1: a sample prepared by dialysis of the purified proS359A against 20 mM Tris-HCl (pH 7.5).

Sample 2: a sample prepared by dialysis of the purified proS359A against 20 mM Tris-HCl (pH 7.5) and addition of EDTA (conc. 1 mM) and guanidine hydrochloride (conc. 6 M), followed by overnight heat-retention at 80° C.

Sample 3: a sample prepared by 5-fold dilution of sample 2 with 20 mM Tris-HCl (pH 7.5) and incubation on ice for 30 minutes.

Sample 4: a sample prepared by overnight dialysis of sample 2 against 20 mM Tris-HCl (pH 7.5).

Figure 14:
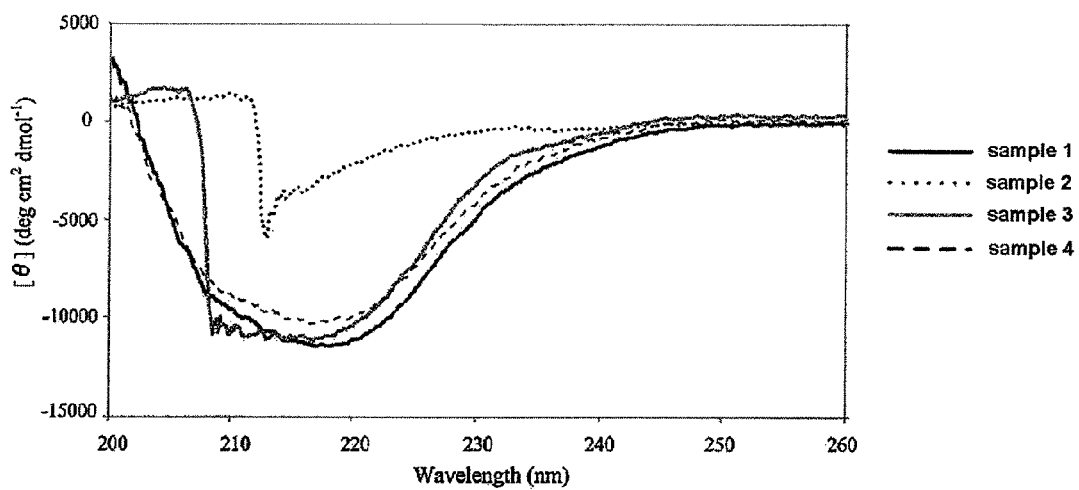
FIG. 14 is a graph showing the examination results on calcium ion requirement for structure formation of the protease of the present invention (Tk-SP).

The results are shown in FIG. 14. As is shown in FIG. 14, compared with the spectrum of sample 1, i.e. the sample which normally formed the secondary structure, the spectrum of sample 2, i.e. the sample which was denatured by addition of guanidine hydrochloride and was under calcium ion-free conditions generated by addition of EDTA, showed a more shallow curve, indicating collapse of the secondary structure resulting in denaturation of the protein. The spectrum of sample 3, i.e. the sample prepared by 5-fold dilution of sample 2 (denatured sample) with the buffer, showed the almost same shape as that of sample 1 except for the range of 200 to 210 nm. The spectrum of sample 4, i.e. the sample prepared by overnight dialysis of sample 2 (denatured sample) against the buffer, showed the completely same curve as that of sample 1. As just described, the secondary structures of sample 3 and sample 4 were recovered, and thus the structure formation of the Tk-SP was shown not to depend on calcium ions.

The above results show that the Tk-SP does not require calcium ions for activation, can exert a stable activity even in detergents containing a chelating agent as an additive, and thus is extremely useful.

The present invention is not limited to the aforementioned embodiments and examples, and various modifications can be made within the scope of the appended claims. Other embodiments provided by suitable combination of technical means disclosed in the different embodiments of the present invention are also within the technical scope of the present invention. All the academic publications and patent literature cited in the above description are incorporated herein by reference.

The invention claimed is:

1. An isolated mature protein having protease activity, consisting of:
   (a) the amino acid sequence of SEQ ID NO: 1, or
   (b) an amino acid sequence having deletion, substitution or addition of one to 10 amino acids in the amino acid sequence of SEQ ID NO: 1.

2. The isolated mature protein having protease activity according to claim 1, wherein the optimum temperature for the protein is 100° C. or higher at a pH of 7 when reacted with azocasein as a substrate for 20 minutes.

3. The isolated mature protein having protease activity according to claim 1, wherein the residual activity of the protein is 40% or more after the protein is treated at 100° C. in 50 mM Tris-HCl at a pH 7 for 90 minutes.

4. The isolated mature protein having protease activity according to claim 1, wherein the residual activity of the protein is 80% or more after the protein is treated at 55° C. in 20 mM Tris-HCl containing 5% sodium dodecyl sulfate at pH 8 for 60 minutes.

5. The isolated mature protein having protease activity according to claim 1, wherein the Km value of the protein is 0.1 to 1 mM when reacted with Suc-AAPF-pNA as a substrate at 80° C.

6. An isolated pro-form of a mature protein having protease activity, consisting of:
   (e) the amino acid sequence of SEQ ID NO: 5, or
   (f) an amino acid sequence having deletion, substitution or addition of one to 10 amino acids in the amino acid sequence of SEQ ID NO 5.

7. A detergent comprising the isolated nature protein according to claim 1.

8. The isolated mature protein according to claim 1, consisting of the amino acid sequence of SEQ ID NO: 3.

* * * * *